US012268392B2

(12) United States Patent
Todd et al.

(10) Patent No.: US 12,268,392 B2
(45) Date of Patent: *Apr. 8, 2025

(54) ANASTOMOSIS DEVICES

(71) Applicant: W. L. Gore & Associates, Inc., Newark, DE (US)

(72) Inventors: Daniel H. Todd, North East, MD (US); Sakthi Sambandam, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 477 days.

This patent is subject to a terminal disclaimer.

(21) Appl. No.: 17/735,291

(22) Filed: May 3, 2022

(65) Prior Publication Data

US 2022/0257252 A1    Aug. 18, 2022

Related U.S. Application Data

(63) Continuation of application No. 15/970,648, filed on May 3, 2018, now Pat. No. 11,344,307, which is a
(Continued)

(51) Int. Cl.
*A61B 17/11* (2006.01)
*A61B 17/00* (2006.01)
(Continued)

(52) U.S. Cl.
CPC ...... *A61B 17/1114* (2013.01); *A61B 17/0057* (2013.01); *A61B 17/11* (2013.01);
(Continued)

(58) Field of Classification Search
CPC ... A61B 17/0057; A61B 17/064; A61B 17/08; A61B 17/083; A61B 17/11;
(Continued)

(56) References Cited

U.S. PATENT DOCUMENTS 3,818,511 A    6/1974   Goldberg et al.
4,119,100 A    10/1978  Rickett
(Continued)

FOREIGN PATENT DOCUMENTS

CN    101374477 A   2/2009
CN    201379668 Y   1/2010
(Continued)

OTHER PUBLICATIONS

International Search Report and Written Opinion from PCT/US2015/028721, mailed Oct. 28, 2015, 13 pages.
(Continued)

*Primary Examiner* — Robert A Lynch

(57) ABSTRACT

Implantable medical devices for connecting tissue layers, such as for connecting a gallbladder and a portion of a gastrointestinal tract to create an anastomosis, include a tubular structure having a plurality of apposition portions, a central region, and a covering material. The devices are endoscopically deployable and may include open cells or undulating edges that facilitate a secure connection between the tissue structures.

24 Claims, 18 Drawing Sheets

Related U.S. Application Data continuation of application No. 14/700,505, filed on Apr. 30, 2015, now Pat. No. 9,993,251.

(60) Provisional application No. 61/987,954, filed on May 2, 2014.

(51) Int. Cl.
*A61B 17/064* (2006.01)
*A61B 17/08* (2006.01)
*A61F 2/06* (2013.01)
*A61F 2/07* (2013.01)
*A61F 2/90* (2013.01)

(52) U.S. Cl.
CPC .................. *A61F 2/06* (2013.01); *A61F 2/90* (2013.01); *A61B 17/064* (2013.01); *A61B 2017/0641* (2013.01); *A61B 17/08* (2013.01); *A61B 17/083* (2013.01); *A61B 2017/1103* (2013.01); *A61B 2017/1107* (2013.01); *A61B 2017/1132* (2013.01); *A61B 2017/1135* (2013.01); *A61B 2017/1139* (2013.01); *A61F 2002/077* (2013.01)

(58) Field of Classification Search
CPC ........ A61B 17/1114; A61B 2017/0641; A61B 2017/1103; A61B 2017/1107; A61B 2017/1132; A61B 2017/1135; A61B 2017/1139; A61F 2/02; A61F 2/04; A61F 2/06; A61F 2/064; A61F 2/07; A61F 2/90; A61F 2002/041; A61F 2002/045; A61F 2002/072; A61F 2002/075; A61F 2002/077

See application file for complete search history.

(56) References Cited

U.S. PATENT DOCUMENTS

| | | | |
|---|---|---|---|
| 4,338,937 A | 7/1982 | Lerman | |
| 4,381,765 A | 5/1983 | Burton | |
| 5,171,259 A | 12/1992 | Inoue | |
| 5,224,953 A | 7/1993 | Morgentaler | |
| 5,261,898 A | 11/1993 | Polin et al. | |
| 5,354,308 A | 10/1994 | Simon et al. | |
| 5,562,728 A | 10/1996 | Lazarus et al. | |
| 5,741,297 A | 4/1998 | Simon | |
| 5,755,778 A | 5/1998 | Kleshinski | |
| 5,797,933 A | 8/1998 | Snow et al. | |
| 5,824,041 A | 10/1998 | Lenker et al. | |
| 5,830,222 A | 11/1998 | Makower | |
| 5,868,783 A | 2/1999 | Tower | |
| 5,945,994 A | 8/1999 | Shimizu et al. | |
| 5,957,949 A | 9/1999 | Leonhardt et al. | |
| 6,007,544 A | 12/1999 | Kim | |
| 6,077,291 A | 6/2000 | Das | |
| 6,120,534 A | 9/2000 | Ruiz | |
| 6,165,209 A | 12/2000 | Patterson et al. | |
| 6,168,617 B1 | 1/2001 | Blaeser et al. | |
| 6,168,621 B1 | 1/2001 | Vrba | |
| 6,171,329 B1 | 1/2001 | Shaw et al. | |
| 6,193,734 B1 | 2/2001 | Bolduc et al. | |
| 6,214,029 B1 | 4/2001 | Thill et al. | |
| 6,217,608 B1 | 4/2001 | Penn et al. | |
| 6,290,728 B1 | 9/2001 | Phelps et al. | |
| 6,315,708 B1 | 11/2001 | Salmon et al. | |
| 6,315,792 B1 | 11/2001 | Armstrong et al. | |
| 6,355,052 B1 | 3/2002 | Neuss et al. | |
| 6,391,036 B1 | 5/2002 | Berg et al. | |
| 6,391,039 B1 | 5/2002 | Nicholas et al. | |
| 6,416,543 B1 | 7/2002 | Hilaire et al. | |
| 6,419,681 B1 | 7/2002 | Vargas et al. | |
| 6,432,127 B1 | 8/2002 | Kim et al. | |
| 6,468,303 B1 | 10/2002 | Amplatz et al. | |
| 6,485,496 B1 | 11/2002 | Suyker et al. | |
| 6,485,507 B1 | 11/2002 | Walak et al. | |
| 6,488,702 B1 | 12/2002 | Besselink | |
| 6,579,314 B1 | 6/2003 | Lombardi et al. | |
| 6,585,758 B1 | 7/2003 | Chouinard et al. | |
| 6,616,675 B1 | 9/2003 | Evard et al. | |
| 6,629,992 B2 | 10/2003 | Bigus et al. | |
| 6,666,883 B1 | 12/2003 | Seguin et al. | |
| 6,712,836 B1 | 3/2004 | Berg et al. | |
| 6,830,575 B2 | 12/2004 | Stenzel et al. | |
| 6,863,684 B2 | 3/2005 | Kim et al. | |
| 6,866,674 B2 | 3/2005 | Galdonik et al. | |
| 6,911,037 B2 | 6/2005 | Gainor et al. | |
| 6,945,994 B2 | 9/2005 | Austin et al. | |
| 6,958,037 B2 | 10/2005 | Ewers et al. | |
| 7,022,131 B1 | 4/2006 | Derowe et al. | |
| 7,025,777 B2 | 4/2006 | Moore | |
| 7,029,482 B1 | 4/2006 | Vargas et al. | |
| 7,037,344 B2 | 5/2006 | Kagan et al. | |
| 7,115,136 B2 | 10/2006 | Park et al. | |
| 7,182,771 B1 | 2/2007 | Houser et al. | |
| 7,223,274 B2 | 5/2007 | Vargas et al. | |
| 7,252,680 B2 | 8/2007 | Freitag | |
| 7,303,569 B2 | 12/2007 | Yencho et al. | |
| 7,431,729 B2 | 10/2008 | Chanduszko | |
| 7,527,644 B2 | 5/2009 | Mangiardi et al. | |
| 7,547,321 B2 | 6/2009 | Silvestri et al. | |
| 7,585,306 B2 | 9/2009 | Abbott et al. | |
| 7,608,086 B2 | 10/2009 | Tanaka et al. | |
| 7,632,302 B2 | 12/2009 | Vreeman et al. | |
| 7,780,686 B2 | 8/2010 | Park et al. | |
| 7,828,814 B2 | 11/2010 | Brenneman et al. | |
| 7,892,247 B2 | 2/2011 | Conston et al. | |
| 7,901,430 B2 | 3/2011 | Matsuura et al. | |
| 8,029,534 B2 | 10/2011 | Hruska et al. | |
| 8,043,360 B2 | 10/2011 | Mcnamara et al. | |
| 8,109,946 B2 | 2/2012 | Cahill et al. | |
| 8,114,125 B2 | 2/2012 | Seibold et al. | |
| 8,197,498 B2 | 6/2012 | Coleman et al. | |
| 8,257,389 B2 | 9/2012 | Chanduszko et al. | |
| 8,262,691 B2 | 9/2012 | Mcguckin et al. | |
| 8,343,088 B2 | 1/2013 | Bates et al. | |
| 8,398,676 B2 | 3/2013 | Roorda et al. | |
| 8,409,167 B2 | 4/2013 | Roschak | |
| 8,425,539 B2 | 4/2013 | Binmoeller et al. | |
| 8,430,934 B2 | 4/2013 | Das | |
| 8,435,284 B2 | 5/2013 | Eidenschink et al. | |
| 8,454,632 B2 | 6/2013 | Binmoeller et al. | |
| 8,579,935 B2 | 11/2013 | Devries et al. | |
| 8,641,747 B2 | 2/2014 | Brenneman et al. | |
| 8,679,171 B2 | 3/2014 | Deem et al. | |
| 8,728,155 B2 | 5/2014 | Montorfano et al. | |
| 8,740,940 B2 | 6/2014 | Maahs et al. | |
| 8,864,813 B2 | 10/2014 | Barr | |
| 8,870,916 B2 | 10/2014 | Ewers et al. | |
| 8,992,604 B2 | 3/2015 | Gross et al. | |
| 9,597,204 B2 | 3/2017 | Benary et al. | |
| 9,668,853 B2 | 6/2017 | Shin | |
| 9,782,533 B2 | 10/2017 | Brenneman et al. | |
| 9,993,251 B2 * | 6/2018 | Todd | A61F 2/06 |
| 10,004,509 B2 | 6/2018 | Todd | |
| 10,363,040 B2 | 7/2019 | Sambandam | |
| 10,806,458 B2 | 10/2020 | Todd | |
| 11,439,396 B2 | 9/2022 | Gore et al. | |
| 11,596,409 B2 | 3/2023 | Todd | |
| 11,712,230 B2 | 8/2023 | Johnson et al. | |
| 11,724,075 B2 | 8/2023 | Johnson | |
| 11,980,367 B2 | 5/2024 | Houghton et al. | |
| 2001/0021872 A1 | 9/2001 | Bailey et al. | |
| 2001/0047180 A1 | 11/2001 | Grudem et al. | |
| 2002/0082627 A1 | 6/2002 | Berg et al. | |
| 2002/0099431 A1 | 7/2002 | Armstrong et al. | |
| 2002/0099437 A1 | 7/2002 | Anson et al. | |
| 2002/0161341 A1 | 10/2002 | Stinson et al. | |
| 2002/0169475 A1 | 11/2002 | Gainor et al. | |
| 2002/0183787 A1 | 12/2002 | Wahr et al. | |
| 2003/0028213 A1 | 2/2003 | Thill et al. | |
| 2003/0032967 A1 | 2/2003 | Park et al. | |
| 2003/0055441 A1 | 3/2003 | Suyker et al. | |

(56) References Cited

U.S. PATENT DOCUMENTS

| | | |
|---|---|---|
| 2003/0069533 A1 | 4/2003 | Kakutani et al. |
| 2003/0093096 A1 | 5/2003 | Mcguckin et al. |
| 2003/0109893 A1 | 6/2003 | Vargas et al. |
| 2003/0120292 A1 | 6/2003 | Park et al. |
| 2003/0139819 A1 | 7/2003 | Beer et al. |
| 2003/0144578 A1 | 7/2003 | Kenneth |
| 2003/0191482 A1 | 10/2003 | Suyker et al. |
| 2003/0225421 A1 | 12/2003 | Peavey et al. |
| 2004/0073155 A1 | 4/2004 | Laufer et al. |
| 2004/0073242 A1 | 4/2004 | Chanduszko |
| 2004/0078053 A1 | 4/2004 | Berg et al. |
| 2004/0092977 A1 | 5/2004 | Vargas et al. |
| 2004/0098105 A1 | 5/2004 | Stinson et al. |
| 2004/0133236 A1 | 7/2004 | Chanduszko |
| 2004/0204755 A1 | 10/2004 | Robin |
| 2004/0211433 A1* | 10/2004 | Albright ............... A61B 17/11 |
| | | 128/898 |
| 2005/0049675 A1 | 3/2005 | Wallace |
| 2005/0055082 A1 | 3/2005 | Ben Muvhar et al. |
| 2005/0070934 A1 | 3/2005 | Tanaka et al. |
| 2005/0070935 A1 | 3/2005 | Ortiz |
| 2005/0070957 A1 | 3/2005 | Das |
| 2005/0149071 A1 | 7/2005 | Abbott et al. |
| 2005/0154465 A1 | 7/2005 | Hodges et al. |
| 2005/0228413 A1 | 10/2005 | Binmoeller et al. |
| 2005/0234509 A1 | 10/2005 | Widomski et al. |
| 2005/0251201 A1 | 11/2005 | Roue et al. |
| 2005/0273124 A1 | 12/2005 | Chanduszko |
| 2005/0288786 A1 | 12/2005 | Chanduszko |
| 2006/0047337 A1 | 3/2006 | Brenneman |
| 2006/0052821 A1 | 3/2006 | Abbott et al. |
| 2006/0106418 A1 | 5/2006 | Seibold et al. |
| 2006/0200228 A1 | 9/2006 | Penn et al. |
| 2006/0212055 A1 | 9/2006 | Karabey et al. |
| 2006/0217761 A1 | 9/2006 | Opolski |
| 2007/0055358 A1 | 3/2007 | Krolik et al. |
| 2007/0073337 A1 | 3/2007 | Abbott et al. |
| 2007/0123917 A1 | 5/2007 | Ortiz et al. |
| 2007/0168014 A1 | 7/2007 | Jimenez et al. |
| 2007/0244518 A1 | 10/2007 | Callaghan |
| 2007/0249985 A1* | 10/2007 | Brenneman .......... A61B 17/083 |
| | | 604/890.1 |
| 2007/0250153 A1 | 10/2007 | Cully et al. |
| 2007/0282430 A1 | 12/2007 | Thommen et al. |
| 2007/0283552 A1 | 12/2007 | Gale et al. |
| 2008/0086168 A1 | 4/2008 | Cahill |
| 2008/0091235 A1 | 4/2008 | Sirota |
| 2008/0243151 A1 | 10/2008 | Binmoeller et al. |
| 2008/0262518 A1 | 10/2008 | Freudenthal |
| 2009/0076541 A1 | 3/2009 | Chin et al. |
| 2009/0090366 A1 | 4/2009 | Cuevas et al. |
| 2009/0093873 A1 | 4/2009 | Navia |
| 2009/0118745 A1 | 5/2009 | Paul, Jr. |
| 2009/0143713 A1 | 6/2009 | Van et al. |
| 2009/0187240 A1 | 7/2009 | Clerc et al. |
| 2009/0216265 A1 | 8/2009 | Devries et al. |
| 2009/0228038 A1 | 9/2009 | Amin |
| 2009/0240316 A1 | 9/2009 | Bruszewski |
| 2009/0270971 A1 | 10/2009 | Xiao et al. |
| 2009/0281557 A1 | 11/2009 | Sander et al. |
| 2010/0010520 A1 | 1/2010 | Takahashi et al. |
| 2010/0023132 A1 | 1/2010 | Imran |
| 2010/0036401 A1 | 2/2010 | Navia |
| 2010/0100105 A1 | 4/2010 | Bates et al. |
| 2010/0106171 A1 | 4/2010 | Arepally et al. |
| 2010/0114128 A1 | 5/2010 | Coleman et al. |
| 2010/0114290 A1 | 5/2010 | Rasmussen et al. |
| 2010/0130995 A1 | 5/2010 | Yevzlin et al. |
| 2010/0168835 A1 | 7/2010 | Dorn |
| 2010/0174253 A1 | 7/2010 | Cline et al. |
| 2010/0234878 A1 | 9/2010 | Hruska et al. |
| 2010/0256548 A1 | 10/2010 | Mcnamara et al. |
| 2010/0268316 A1 | 10/2010 | Brenneman et al. |
| 2010/0305590 A1* | 12/2010 | Holmes ............... A61F 5/0079 |
| | | 606/151 |
| 2010/0331953 A1 | 12/2010 | Matsuoka et al. |
| 2011/0040366 A1 | 2/2011 | Goetz et al. |
| 2011/0054381 A1 | 3/2011 | Van et al. |
| 2011/0060398 A1 | 3/2011 | Tupil et al. |
| 2011/0118765 A1 | 5/2011 | Aguirre |
| 2011/0125244 A1 | 5/2011 | Roeder et al. |
| 2011/0137410 A1 | 6/2011 | Hacohen |
| 2011/0213415 A1 | 9/2011 | Mcguckin et al. |
| 2011/0218609 A1 | 9/2011 | Chobotov et al. |
| 2011/0257461 A1 | 10/2011 | Lipperman et al. |
| 2011/0257723 A1 | 10/2011 | Mcnamara |
| 2011/0301689 A1 | 12/2011 | Dorn et al. |
| 2012/0065652 A1 | 3/2012 | Cully et al. |
| 2012/0089216 A1 | 4/2012 | Rapaport et al. |
| 2012/0130417 A1 | 5/2012 | Lepulu et al. |
| 2012/0172927 A1* | 7/2012 | Campbell ........ A61B 17/12172 |
| | | 606/213 |
| 2012/0232505 A1 | 9/2012 | Eskaros et al. |
| 2012/0241503 A1 | 9/2012 | Baxter, III et al. |
| 2012/0283811 A1 | 11/2012 | Neilan |
| 2013/0012969 A1 | 1/2013 | Shin |
| 2013/0030351 A1 | 1/2013 | Belhe et al. |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0096606 A1 | 4/2013 | Bruchman et al. |
| 2013/0165967 A1 | 6/2013 | Amin et al. |
| 2013/0197623 A1 | 8/2013 | Mchugo |
| 2013/0218192 A1 | 8/2013 | Erzberger et al. |
| 2013/0245742 A1 | 9/2013 | Norris |
| 2013/0261531 A1 | 10/2013 | Gallagher et al. |
| 2013/0317546 A1 | 11/2013 | Brown |
| 2014/0012368 A1 | 1/2014 | Sugimoto et al. |
| 2014/0031842 A1 | 1/2014 | Brenneman et al. |
| 2014/0074155 A1 | 3/2014 | Rothstein et al. |
| 2014/0236064 A1 | 8/2014 | Binmoeller et al. |
| 2014/0303710 A1 | 10/2014 | Zhang et al. |
| 2014/0343602 A1 | 11/2014 | Cox et al. |
| 2015/0005810 A1 | 1/2015 | Center et al. |
| 2015/0039084 A1 | 2/2015 | Levi et al. |
| 2015/0066077 A1 | 3/2015 | Akpinar |
| 2015/0250630 A1 | 9/2015 | Irwin et al. |
| 2015/0265437 A1 | 9/2015 | Fleury et al. |
| 2015/0313595 A1 | 11/2015 | Houghton et al. |
| 2015/0313598 A1 | 11/2015 | Todd et al. |
| 2015/0313599 A1 | 11/2015 | Johnson et al. |
| 2015/0313738 A1 | 11/2015 | Cully et al. |
| 2016/0045199 A1 | 2/2016 | Mooney |
| 2016/0074023 A1 | 3/2016 | Sakamoto et al. |
| 2016/0135813 A1 | 5/2016 | Johnson et al. |
| 2016/0256169 A1 | 9/2016 | Ben-Muvhar et al. |
| 2017/0020498 A1 | 1/2017 | Blom |
| 2017/0105854 A1 | 4/2017 | Treacy et al. |
| 2018/0221194 A1 | 8/2018 | Eskaros et al. |
| 2018/0242972 A1 | 8/2018 | Todd |
| 2018/0250009 A1 | 9/2018 | Todd et al. |
| 2018/0296809 A1 | 10/2018 | Johnson |
| 2019/0298909 A1 | 10/2019 | Cully et al. |
| 2020/0015823 A1 | 1/2020 | Sambandam |
| 2020/0146680 A1 | 5/2020 | Houghton et al. |
| 2021/0085328 A1 | 3/2021 | Todd |
| 2022/0370071 A1 | 11/2022 | Johnson et al. |
| 2023/0255632 A1 | 8/2023 | Todd |
| 2023/0320714 A1 | 10/2023 | Johnson et al. |
| 2023/0338714 A1 | 10/2023 | Johnson |
| 2024/0252175 A1 | 8/2024 | Houghton et al. |

FOREIGN PATENT DOCUMENTS

| | | |
|---|---|---|
| CN | 101951983 A | 1/2011 |
| CN | 102083391 A | 6/2011 |
| CN | 102395323 A | 3/2012 |
| CN | 102802539 A | 11/2012 |
| CN | 202801864 U | 3/2013 |
| CN | 103200975 A | 7/2013 |
| CN | 103209649 A | 7/2013 |
| CN | 103313681 A | 9/2013 |
| CN | 103598902 A | 2/2014 |
| CN | 103945775 A | 7/2014 |

(56) References Cited

FOREIGN PATENT DOCUMENTS

| | | |
|---|---|---|
| CN | 104168839 A | 11/2014 |
| CN | 104244843 A | 12/2014 |
| CN | 104519838 A | 4/2015 |
| CN | 104968284 A | 10/2015 |
| CN | 106413586 A | 2/2017 |
| DE | 10148185 A1 | 4/2003 |
| EP | 0991375 A1 | 4/2000 |
| EP | 1790297 A1 | 5/2007 |
| EP | 1872741 A1 | 1/2008 |
| EP | 1480565 B1 | 12/2008 |
| EP | 2543323 A1 | 1/2013 |
| EP | 3136982 A2 | 3/2017 |
| EP | 3136984 A1 | 3/2017 |
| GB | 2409978 A | 7/2005 |
| JP | 2000-505316 A | 5/2000 |
| JP | 2001-501493 A | 2/2001 |
| JP | 2001-520908 A | 11/2001 |
| JP | 2001-340346 A | 12/2001 |
| JP | 2003-527939 A | 9/2003 |
| JP | 2004-049806 A | 2/2004 |
| JP | 2005-503881 A | 2/2005 |
| JP | 2005-518863 A | 6/2005 |
| JP | 2005-528181 A | 9/2005 |
| JP | 2005-534390 A | 11/2005 |
| JP | 2006-006648 A | 1/2006 |
| JP | 2007-097620 A | 4/2007 |
| JP | 2007-530128 A | 11/2007 |
| JP | 2009-000535 A | 1/2009 |
| JP | 2009-508641 A | 3/2009 |
| JP | 2009-518149 A | 5/2009 |
| JP | 2010-523209 A | 7/2010 |
| JP | 2010-528821 A | 8/2010 |
| JP | 2010-188189 A | 9/2010 |
| JP | 2011-509758 A | 3/2011 |
| JP | 2011-519709 A | 7/2011 |
| JP | 2012-513783 A | 6/2012 |
| JP | 2013-013715 A | 1/2013 |
| JP | 2014-503246 A | 2/2014 |
| JP | 2015-500665 A | 1/2015 |
| JP | 2015-513926 A | 5/2015 |
| JP | 2021-155586 A | 10/2021 |
| JP | 2021-192846 A | 12/2021 |
| WO | 97/27898 A1 | 8/1997 |
| WO | 97/32543 A1 | 9/1997 |
| WO | 98/02099 A1 | 1/1998 |
| WO | 98/08462 A2 | 3/1998 |
| WO | 98/16174 A1 | 4/1998 |
| WO | 98/58600 A1 | 12/1998 |
| WO | 99/38454 A2 | 8/1999 |
| WO | 01/72367 A1 | 10/2001 |
| WO | 02/83038 A2 | 10/2002 |
| WO | 2003/028522 A2 | 4/2003 |
| WO | 03/73944 A1 | 9/2003 |
| WO | 2003/103476 A2 | 12/2003 |
| WO | 2004/012603 A2 | 2/2004 |
| WO | 2004/087236 A2 | 10/2004 |
| WO | 2005/089655 A1 | 9/2005 |
| WO | 2006/121855 A2 | 11/2006 |
| WO | 2007/024964 A1 | 3/2007 |
| WO | 2007/053243 A2 | 5/2007 |
| WO | 2007/100970 A2 | 9/2007 |
| WO | 2008/124314 A1 | 10/2008 |
| WO | 2008/157172 A1 | 12/2008 |
| WO | 2009/082718 A1 | 7/2009 |
| WO | 2009/091899 A2 | 7/2009 |
| WO | 2009/109348 A1 | 9/2009 |
| WO | 2009/140195 A1 | 11/2009 |
| WO | 2009/146369 A1 | 12/2009 |
| WO | 2010/076052 A1 | 7/2010 |
| WO | 2010/129162 A1 | 11/2010 |
| WO | 2012/034108 A1 | 3/2012 |
| WO | 2012/067912 A1 | 5/2012 |
| WO | 2012/071075 A1 | 5/2012 |
| WO | 2013/137977 A1 | 9/2013 |
| WO | 2013/152891 A2 | 10/2013 |
| WO | 2015/168501 A2 | 11/2015 |
| WO | 2015/168504 A2 | 11/2015 |
| WO | 2015/168506 A1 | 11/2015 |
| WO | 2015/168507 A1 | 11/2015 |
| WO | 2015/168508 A2 | 11/2015 |

OTHER PUBLICATIONS

European Search Report for EP Patent Application No. 24153796.8, Issued on Apr. 30, 2024, 7 pages.

* cited by examiner

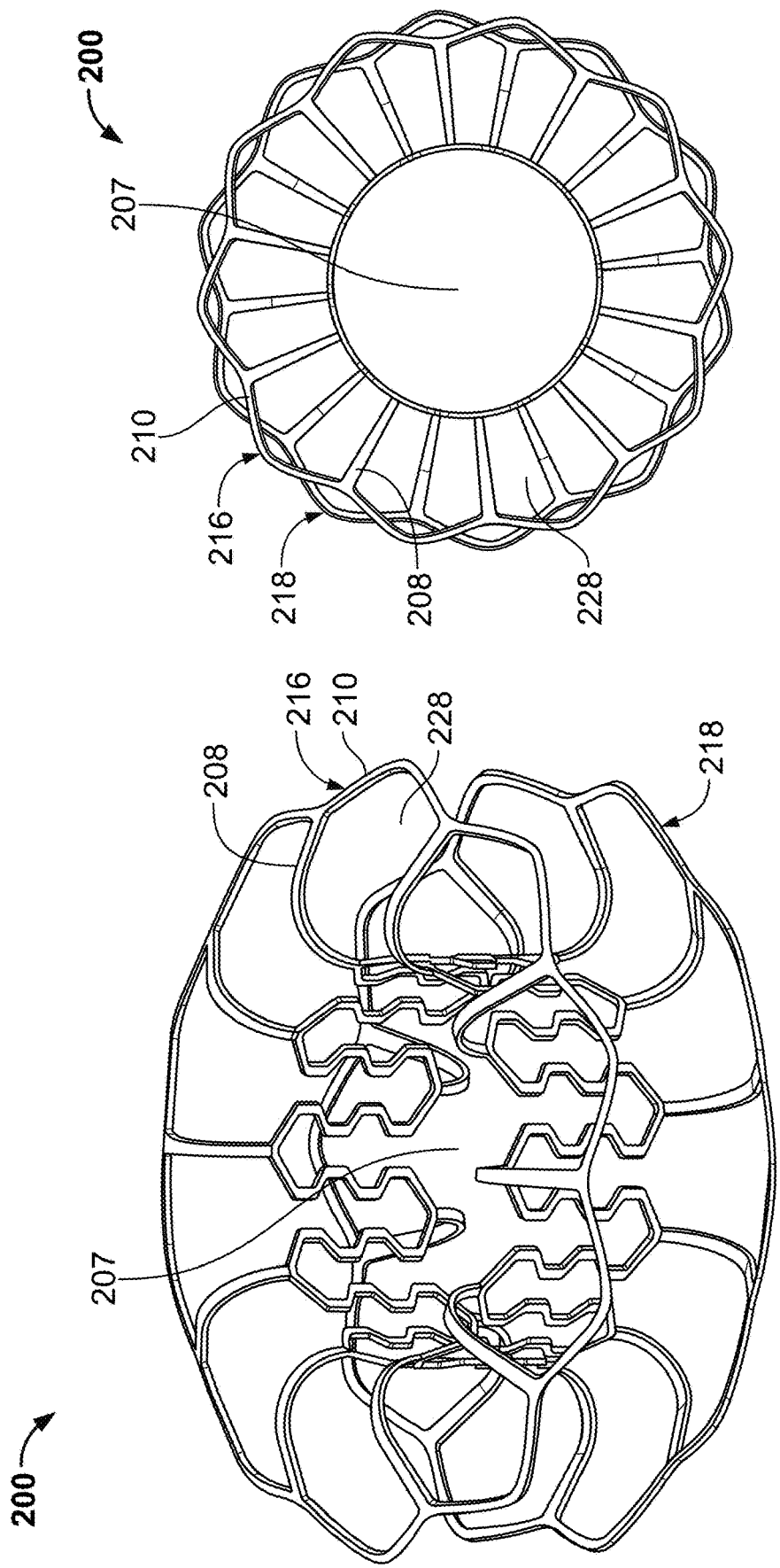

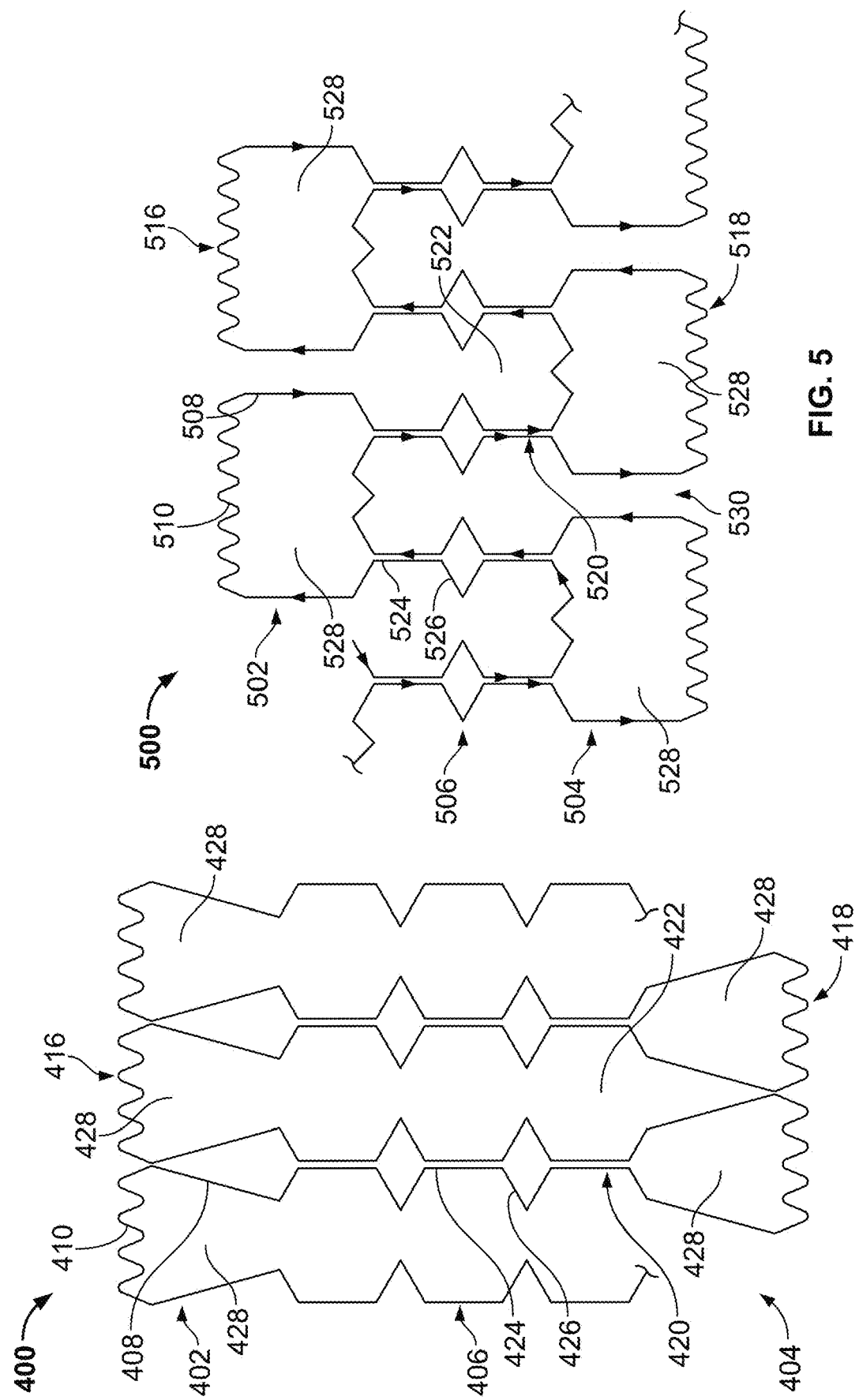

ANASTOMOSIS DEVICES

CROSS-REFERENCE TO RELATED APPLICATION

This application is a continuation of U.S. patent application Ser. No. 15/970,648, filed May 3, 2018, which is a continuation of U.S. patent application Ser. No. 14/700,505, filed Apr. 30, 2015, now U.S. Pat. No. 9,993,251, issued Jun. 12, 2018, which claims the benefit of U.S. Provisional Application 61/987,954, filed May 2, 2014, which are incorporated herein by reference in their entireties for all purposes.

FIELD

This disclosure relates generally to implantable medical devices, and more specifically, to implantable devices for connecting tissue layers to create an anastomosis. A method of implanting an anastomosis in a patient is also provided.

BACKGROUND

An anastomosis is a surgical connection between two tissue structures, such as blood vessels or intestines. For example, in the context of coronary artery bypass graft surgery, a graft vessel is anastomosed to a native coronary artery so that blood can flow through the graft vessel.

Anastomoses can be created in various manners including, but not limited to: end-to-end, end-to-side, and side-to-side anastomoses. Often, suturing is used to create such anastomoses.

SUMMARY

One aspect of the invention relates to an implantable medical device for creating an anastomosis that includes a tubular structure that includes at least one elongate member forming a framework of interconnected struts. The tubular structure includes (1) a central portion defining a longitudinal axis, the central portion including a plurality of central portion cells defined by the elongate member, (2) a first apposition portion at a first end of the central portion, the first apposition portion including a plurality of first flange cells defined by the elongate member, and (3) a second apposition portion at a second end of the central portion, the second apposition portion including a plurality of second flange cells defined by the elongate member. At least some of the second flange cells are closed at a first end by an undulating portion of the elongate member and opened at a second end to the central portion. In at least one exemplary embodiment, the elongate member forms (1) a first pattern extending longitudinally along the central portion, (2) a first flange cell of the plurality of first flange cells, (3) a second pattern extending longitudinally along the central portion and opposing the first pattern, and (4) a second flange cell of the plurality of second flange cells. In some embodiments a single elongate member forms the central portion, the first apposition portion, and the second apposition portion. In other embodiments, the central portion cells are open to longitudinally-adjacent central portion cells and are closed to circumferentially-adjacent central portion cells. In further embodiments, each of the plurality of second flange cells is open to one or more of the central portion cells of the plurality of central portion cells.

A second aspect of the invention relates to an implantable medical device for creating an anastomosis. The device includes a tubular structure including at least one elongate member forming a framework of interconnected struts. The tubular structure includes (1) a central portion having a plurality of body cells defined by the elongate member, (2) a first apposition portion at a first end of the central portion having a plurality of first flange cells defined by the elongate member, and (3) a second apposition portion at a second end of the central portion having a plurality of second flange cells defined by the elongate member. The elongate member may be formed such that (1) the elongate member forms a first pattern traversing the central portion along a longitudinal axis, (2) the elongate member defines a first flange cell of the first plurality of flange cells, (3) the elongate member traverses the central portion along the longitudinal axis in a second pattern opposing the first pattern, and (4) the elongate member defines a second flange cell of the second plurality of flange cells. In at least one embodiment, each successive flange cell of the first and second plurality of flange cells is out of phase with directly preceding flange cells of the first and second plurality of flange cells. Additionally, the body cells may be open to longitudinally-adjacent body cells and may be closed to circumferentially-adjacent body cells. In some embodiments, each of the plurality of first flange cells may be open to the body and each of the plurality of second flange cells may be open to the body.

A third aspect of the invention relates to a method of implanting an anastomosis device in a patient that includes (1) navigating a delivery sheath containing the anastomosis device to a target location within the patient and (2) deploying the anastomosis device from the delivery sheath such that at least one layer of tissue is between the first apposition portion and the second apposition portion. The anastomosis device includes a tubular structure that includes at least one elongate member forming a framework of interconnected struts. The tubular structure includes (1) a central portion that includes a plurality of body cells defined by the elongate member, (2) a first apposition portion at a first end of the central portion having a plurality of first flange cells defined by the elongate member such that the plurality of first flange cells are open to the central portion, and (3) a second apposition portion at a second end of the central portion that includes a plurality of second flange cells defined by the elongate member such that the plurality of second flange cells are open to the central portion.

DESCRIPTION OF DRAWINGS

The accompanying drawings are included to provide a further understanding of the disclosure and are incorporated in and constitute a part of this specification, illustrate embodiments, and together with the description serve to explain the principles of the disclosure.

FIG. 2B is a perspective view of the anastomosis device of FIG. 2A;

FIG. 2C is an end view of the anastomosis device of FIG. 2A;

FIG. 4 is a flat pattern of an anastomosis device in accordance with some embodiments;

FIG. 5 is a flat pattern of an anastomosis device in accordance with some embodiments;

DETAILED DESCRIPTION

Figure 1:
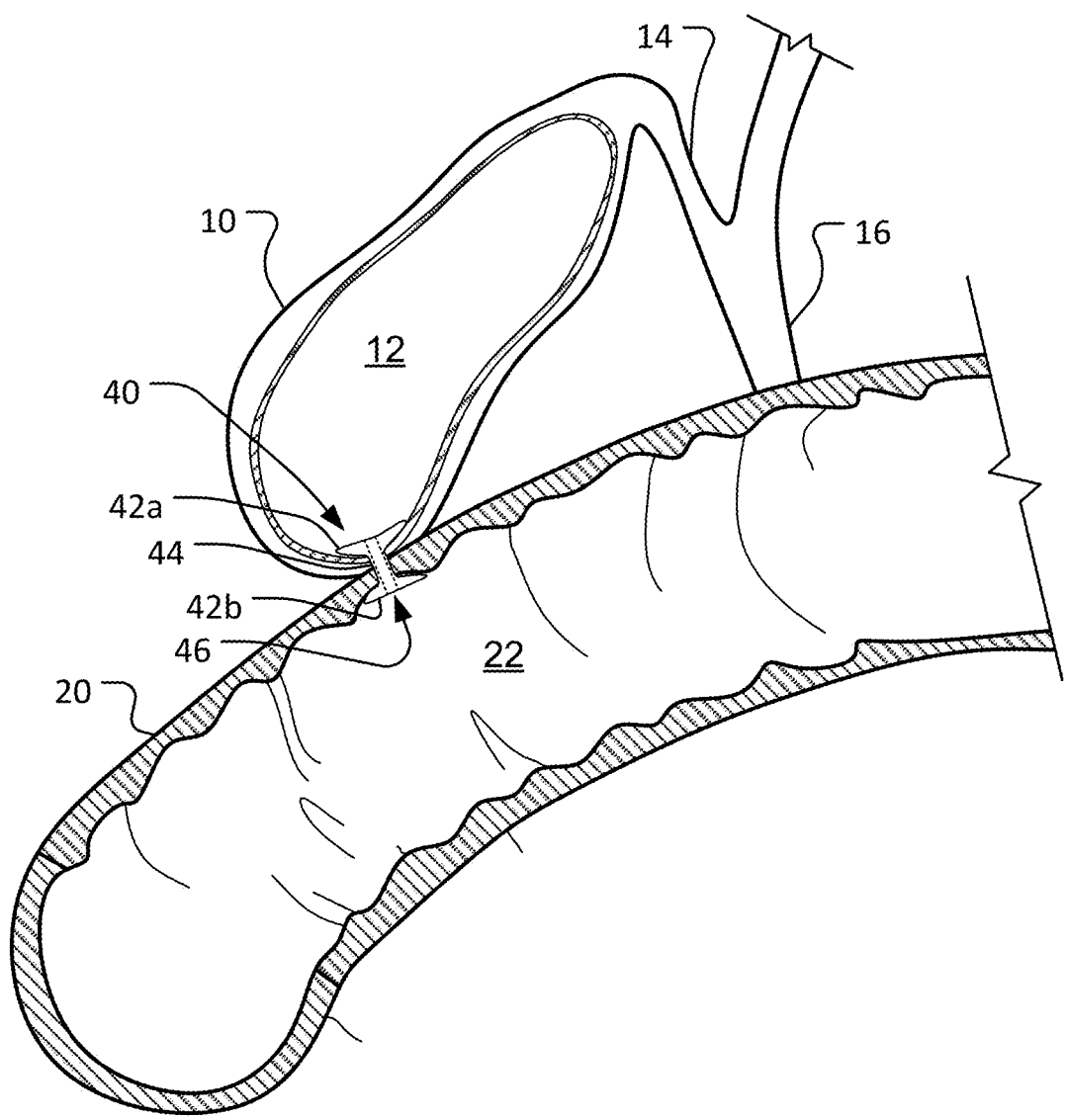
FIG. 1 is a cutaway perspective view of an exemplary anastomosis device that has been implanted within a patient to act as a shunt between the patient's gallbladder and intestine in accordance with some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present disclosure is directed to implantable devices for connecting tissue layers, for example, to circumvent a conduit or organ blockage, such as by creating a direct passage between tissue structures (e.g. connecting a gallbladder and a portion of a gastrointestinal tract) to create an anastomosis that facilitates material flow therebetween. The devices described herein are endoscopically deployable or deliverable via a catheter and may include self-expanding apposition mechanisms that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein are configured to be removable after implantation. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed. The devices described herein can provide alternative treatments for patients who are not suitable candidates for other types of treatments (e.g., gallbladder removal surgery) and/or to avoid known complications of other types of treatments (e.g., external biliary drainage).

This disclosure refers to anastomosis devices in an exemplary fashion. That is, it should be understood that the inventive concepts disclosed in this disclosure can also be applied to other types of devices. For example, this disclosure also provides implantable devices that, in some embodiments, can be used for occluding tissue structures, organs, body conduits, blood vessels, the GI tract, and the like. For example, in some embodiments the devices provided herein can be used to occlude septal defects. In other embodiments, the devices provided herein can be used to occlude a patient's vasculature or GI tract. In some such embodiments, the device does not include a tunnel or central aperture through the device. Rather, in some embodiments a covering material seals the device to inhibit, modulate, or substantially prevent material from flowing through the device.

Referring to FIG. 1, an exemplary anastomosis device 40 in accordance with some embodiments provided herein that can be implanted in a patient to create a fluidic connection between two organs, spaces, tissue structures, conduits, and the like, and combinations thereof is shown. For example, in the depicted implementation the anastomosis device 40 is connecting a gallbladder 10 (that defines an internal gallbladder space 12) with an intestine 20 (that defines an internal intestinal space 22). Hence, the anastomosis device 40 is acting as a fluidic shunt device between the internal gallbladder space 12 and the internal intestinal space 22. Such an implementation may provide a beneficial treatment to the patient when, for example, a flow blockage exists in the native anatomical conduits connecting the internal gallbladder space 12 and the internal intestinal space 22. For example, in some instances the patient may have one or more gallstones that cause a blockage of the patient's cystic duct 14 and/or common bile duct 16. In such a case, the anastomosis device 40 can provide a fluidic passageway such that bile from the gallbladder 10 can flow into the intestine 20. If not for the anastomosis device 40, when bile is blocked from flowing out of the gallbladder 10 cholecystitis (inflammation of the gallbladder 10) may result.

While the anastomosis devices provided herein can be used in some implementations to relieve or prevent cholecystitis as described above, it should be understood that the anastomosis devices provided herein can also be used in many other types of implementations within a patient. For example, the anastomosis devices provided herein can be used in conjunction with various body tissue structures and organs such as, but not limited to, stomachs, colons, small intestines, pancreases, blood vessels, bladders, kidneys, conduits, and the like.

In general, some embodiments of the anastomosis devices provided herein (of which anastomosis device 40 is one type of example), include a first tissue apposition portion 42a, a second tissue apposition portion 42b, and a central portion 44 therebetween. The central portion 44 defines a lumen 46 that extends longitudinally from a first end of the anastomosis device 40 to a second end of the device 40. The lumen 46 acts as a connection (e.g., a shunt passageway) between the internal gallbladder space 12 and the internal intestinal space 22, such that the internal gallbladder space 12 is in fluid communication with the internal intestinal space 22 via the anastomosis device 40.

Referring to FIGS. 2A-2E, an exemplary anastomosis device 200 that includes a framework of elongate elements that define a first apposition portion 202, a second apposition portion 204, and a central portion 206 is depicted. In some embodiments, the anastomosis device 200 can be a type of stent device, which can refer broadly to devices that include a framework of elongate elements and include devices such as, but not limited to, anastomosis devices. The central portion 206 is disposed between and interconnects the first apposition portion 202 and the second apposition portion 204. A covering material (not shown in FIGS. 2A-2E) can be disposed on at least some portions of the framework. Such covering materials (e.g., covering material and others described below) may also be referred to herein merely as a covering.

In some embodiments, the central portion 206 can form a body that defines a lumen 207 that extends between the first apposition portion 202 and the second apposition portion 204. The first and second apposition portions 202 and 204 can form flanges extending substantially radially outward from opposite ends of the central portion 206. In some embodiments, the lumen 207 provides an anastomosis passageway or tunnel through which biological materials or fluids can pass. The device 200 is shown in an expanded configuration (also referred to herein as a deployed configuration). The expanded or deployed configuration is the configuration that the device 200 naturally exhibits in the absence of external forces acting upon the device 200. It should be understood that when the anastomosis device 200 is implanted in a patient, the configuration of the device 200 may be somewhat different than shown because of the external forces from the patient's anatomy that are exerted on the device 200.

In some embodiments, the first apposition portion 202, the second apposition portion 204, and the central portion 206 are formed of elongate elements such as spring wire (e.g., L605 steel or stainless steels), shape memory alloy wire (e.g., nitinol or nitinol alloys), super-elastic alloy wire (e.g., nitinol or nitinol alloys), or other suitable types of elongate elements or wires, or combinations thereof. In some such embodiments, the first apposition portion 202, the second apposition portion 204, and the central portion 206 can be formed from the same piece of precursor material that is cut to create the framework of elongate elements. In some such embodiments, the precursor material is a tubular material or a sheet material. In some embodiments, different types of elongate elements are used at different locations of the first apposition portion 202, the second apposition portion 204, and/or the central portion 206. In some embodiments, the elongate elements of the first apposition portion 202, the second apposition portion 204, and the central portion 206 (or portions thereof) may be constructed of polymeric materials.

Suitable materials for the elongate elements of the devices provided herein include a variety of metallic materials including alloys exhibiting, shape memory, elastic and super-elastic characteristics. Shape memory refers to the ability of a material to revert to an originally memorized shape after plastic deformation by heating above a critical temperature. Elasticity is the ability of a material to deform under load and return or substantially return to its original shape when the load is released. Most metals will deform elastically up to a small amount of strain. Super-elasticity refers to the ability of a material to deform under strain to much larger degree than typical elastic alloys, without having this deformation become permanent. For example, the super-elastic materials included in the frames of some anastomosis device embodiments provided herein are able to withstand a significant amount of bending and flexing and then return or substantially return to the frame's original form without deformation. In some embodiments, suitable elastic materials include various stainless steels which have been physically, chemically, and otherwise treated to produce a high springiness, metal alloys such as cobalt chrome alloys (e.g., ELGILOY™, MP35N, L605), platinum/tungsten alloys. Embodiments of shape memory and super-elastic alloys include the NiTi alloys, ternary shape memory alloys such as NiTiPt, NiTiCo, NiTiCr, or other shape memory alloys such as copper-based shape memory alloys. Additional materials could combine both shape memory and elastic alloys such as a drawn filled tube where the outer layer is constructed of nitinol and the inner core is a radiopaque material such as platinum or tantalum. In such a construct, the outer layer provides the super-elastic properties and the inner core remains elastic due to lower bending stresses.

In some embodiments, the elongate elements used to construct the devices provided herein can be treated in various ways to increase the radiopacity of the devices for enhanced radiographic visualization. In some embodiments, the devices are at least partially a drawn-filled type of NiTi containing a different material at the core, such as a material with enhanced radiopacity. In some embodiments, the devices include a radiopaque cladding or plating on at least portions of the first apposition portion, the second apposition portion, and the central portion. In some embodiments, one or more radiopaque markers are attached to the devices. In some embodiments, the elongate elements and/or other portions of the devices provided herein are also visible via ultrasound.

In some embodiments, the first apposition portion 202, the second apposition portion 204, and the central portion 206, comprise a framework of interconnected elongate elements that is constructed by cutting a tube. In one such embodiment, a tube of metallic material (e.g., nitinol, stainless steel, cobalt, etc.) is laser cut, and then the tube is expanded and shaped into the desired configuration. In some such embodiments, the metallic material is shape-set in the desired configuration so that the material receives a shape-memory whereby the material will naturally strive to attain the desired configuration. In some embodiments, shape memory materials such as nitinol may strive to attain the desired configuration when exposed to body temperature.

As described in more detail below, in some embodiments a covering material can be disposed on or around some portions, or on or around all of the first apposition portion 202, the second apposition portion 204, and/or the central portion 206. In some embodiments, portions of the first apposition portion 202, the second apposition portion 204, and/or the central portion 206 can remain free of the covering material. In some embodiments, no covering material is included on the anastomosis device 200.

The first apposition portion 202 and the second apposition portion 204 each include a plurality of struts 208. In some embodiments, the struts 208 of each of the first and second apposition portions 202 and 204 are configured to form, in a general sense, flanges that contact tissue surfaces. More particularly, the first apposition portion 202 and the second apposition portion 204 are configured to engage one or more layers of tissue therebetween, and to provide apposition forces against the tissue surfaces. The apposition forces provided by the first and second apposition portions 202 and 204 can facilitate fixation of the device 200 to the tissue and provide migration resistance such that the device 200 can reliably remain positioned at a target site in a patient as desired.

In some embodiments, the materials and configuration of the anastomosis device 200 (and the other anastomosis device embodiments provided herein) allow the devices to be elastically crushed, folded, and/or collapsed into a low-profile delivery configuration for containment within a lumen for transcatheter or endoscopic/thorascopic delivery, and to self-expand to an operative size and configuration once positioned at a desired target site within a body and deployed from the lumen. For example, the anastomosis device 200 can be configured in a collapsed delivery configuration in which the plurality of struts 208 are radially compressed such that they are forced to extend substantially parallel to the axis of the central portion 206, and in which the diameter of the central portion 206 is also crushed to become smaller. Due to the use of such materials and structure, the device 200 may also exhibit, for example, beneficial fatigue resistance and elastic properties.

After deployment, the plurality of struts 208 extend from the central portion 206 at a radial orientation and geometry to exert a desired level of apposition pressure on the tissue. In some embodiments, the plurality of struts 208 extend from the central portion 206 such that the nominal measure of the angle between the struts 208 and the longitudinal axis of the device 200 is about 100°, or about 90°, or about 80°, or about 70°, or about 60°, or about 50°, or about 40°, or about 30°, or about 20°, or about 10°, and the like.

Still referring to FIGS. 2A-2E, in some embodiments of the anastomosis device 200 (and in some embodiments of the other anastomosis devices provided herein) the plurality of struts 208 are interconnected by connecting members 210. The connecting members 210 are shown in deployed configurations in which the connecting members 210 are arranged in a series of undulations—each having a vertex 214 extending towards the central portion 206 and a vertex 215 extending away from the central portion 206. In some embodiments, the struts 208 can connect to the connecting members 210 at the vertex 214. In other embodiments, the struts 208 can connect to the connecting members 210 at the vertex 215.

In some embodiments, the connecting members 210 serve to support and stabilize the struts 208 to thereby cause the apposition portions 202 and 204 to have a more rigid construct. In some such embodiments, the apposition portions 202 and 204 can exert a greater level of apposition pressure while maintain a compliancy by which the apposition portions 202 and 204 can conform to the anatomical topography of the tissue. In addition, the sealing capabilities of the apposition portions 202 and 204 may be enhanced. In some embodiments, the stability and support provided by the connecting member 210 serves to increase the apposition force provided against the gallbladder or provided against the portion of the gastrointestinal tract, for example.

Figure 2A:
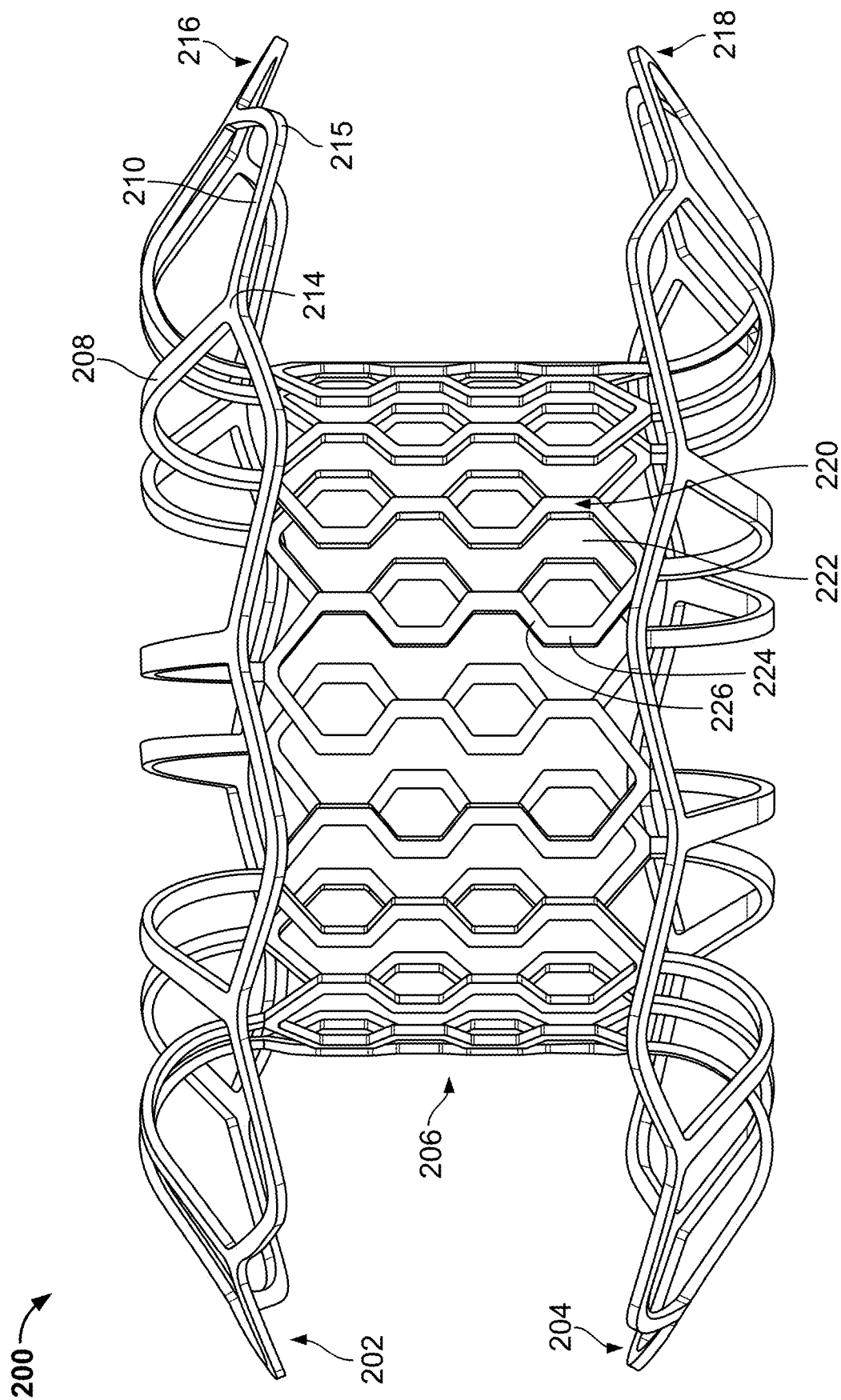
FIG. 2A is a side view of an exemplary anastomosis device in accordance with some embodiments.

In some embodiments, the connecting members 210 combine to form circumferential rings 216 and 218 extending circumferentially around a radially-outer circumference of each of the first and second apposition portions 202 and 204, respectively. The circumferential rings 216 and 218 can have a shape that is wavy or that undulates circumferentially around edges of the first and second apposition portions 202 and 204. In some embodiments, the circumferential rings 216 and 218 can have a shape that undulates in an axial direction, as can be seen in FIG. 2A. In some embodiments, the circumferential rings 216 and 218 can have a shape that undulates in a radial direction, as can be seen in FIG. 2C. In some embodiments, the circumferential rings 216 and 218 can have a shape that undulates in both axial and radial directions. In some embodiments, the circumferential rings 216 and 218 can undulate sinusoidally around the edges of one or both of the first and second apposition portions 202 and 204. Forming one or both of the circumferential rings 216 and 218 with a sinusoidal, serpentine, or otherwise undulating shape can increase an amount of surface area of contact between the first and second apposition portions 202 and 204 and tissue, thus reducing force at a given location on that tissue.

The central portion 206 can include a series of body struts 220, each extending longitudinally and forming the central body 206 of the anastomosis device 200. The body struts 220 define body cells 222 of the central portion 206 and separate the respective body cells 222 from circumferentially-adjacent body cells 222. In some embodiments, each of the body struts 220 can include a plurality of axially-extending portions 224 interconnected with a plurality of angled portions 226. This can allow the body struts 220 to create a relatively strong central portion 206 without necessarily interconnecting the body struts 220 across the body cells 222 at several locations along the length of the body struts 220.

Figure 2E:
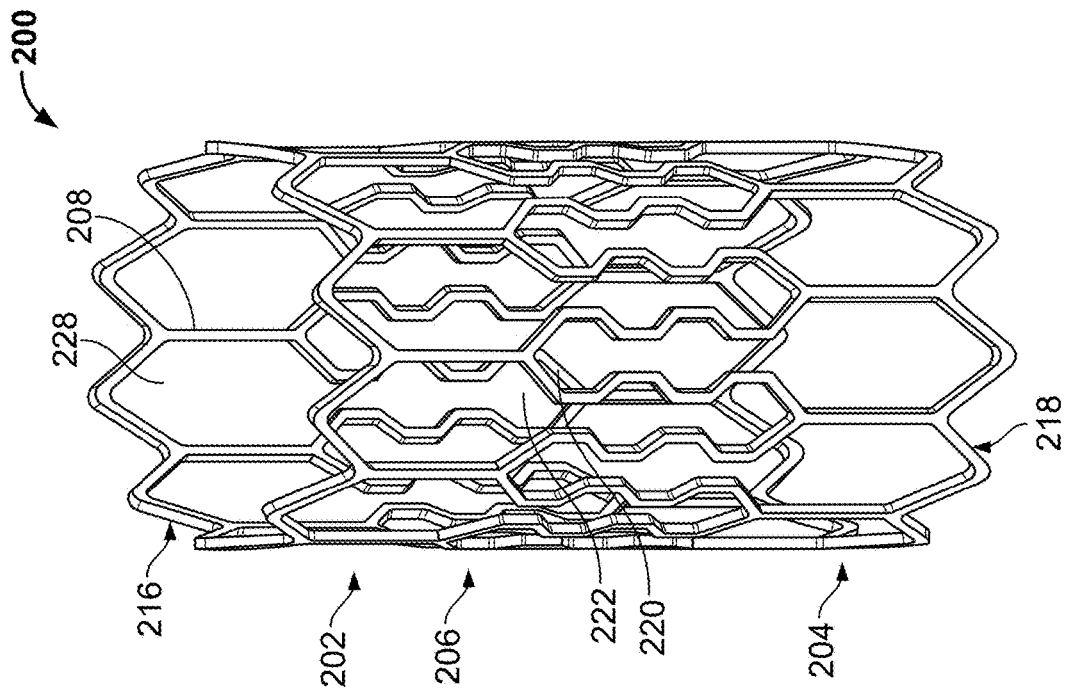
FIG. 2E is a perspective view of the anastomosis device of FIG. 2A prior to forming flanges.
Figure 2D:
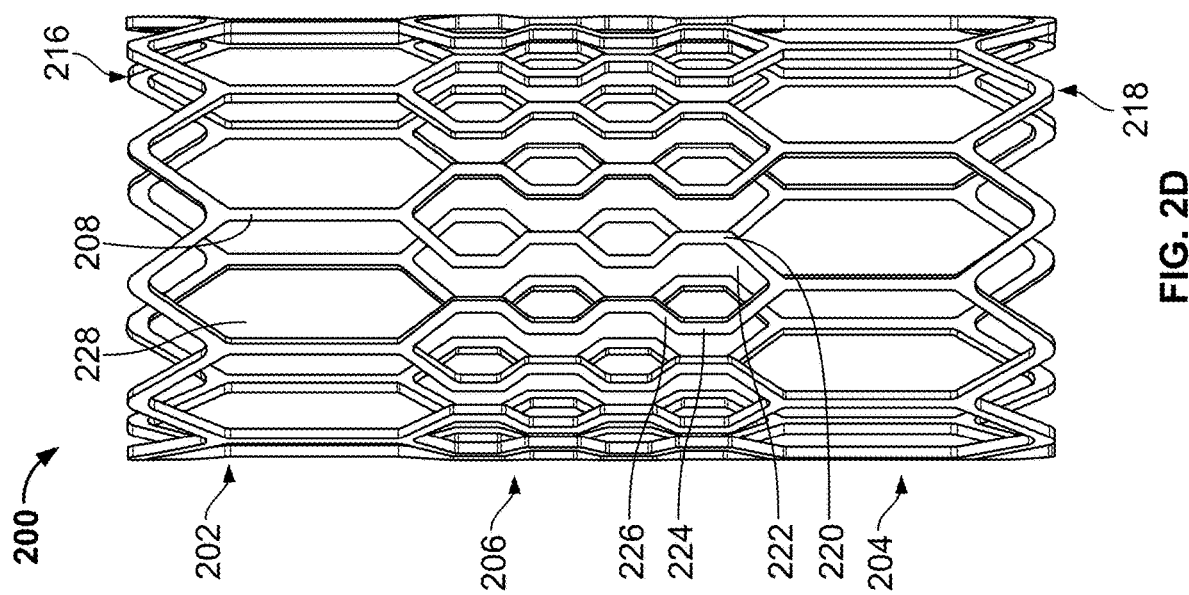
FIG. 2D is a side view of the anastomosis device of FIG. 2A prior to forming flanges.

The struts 208 of the apposition portions 202 and 204 can define flange cells 228 between the struts 208. The flange cells 228 can be open cells, with no strut separating the flange cells 228 from the central portion 206. As shown in FIGS. 2B, 2D, and 2E, the flange cells 228 are closed at a distal-most end of the flange cells 228 by connecting members 210 and are open at a center-most end of the flange cells 228, such that the flange cells 228 are open to the body cells 222.

FIGS. 2D and 2E show the anastomosis device 200 in a partially-formed configuration, prior to forming the anastomosis device 200 in the shape illustrated in FIGS. 2A, 2B, and 2C. As shown in FIGS. 2D and 2E, the anastomosis device 200 can have a substantially cylindrical shape in the partially-formed configuration, with the struts 208 extending substantially parallel to the body struts 220. The anastomosis device 200 can be shaped in a manufacturing process, such as, for example, that described with respect to FIG. 10 (below), to transform the anastomosis device 200 from the pre-formed configuration shown in FIGS. 2D and 2E to the final configuration shown in FIGS. 2A, 2B, and 2C.

In some embodiments, the anastomosis device 200 can be formed in a manner such that an elongate member forms a first pattern traversing the central portion 206 along a longitudinal axis, the elongate member defines a first flange cell 228 of the first apposition portion 202, the elongate member traverses the central portion 206 along the longitudinal axis in a second pattern opposing the first pattern, the elongate member defines a second opposing flange cell 228, and the elongate member then repeats those winding steps to form additional patterns of the central portion 206 and flanges cells 228 of the anastomosis device 200.

In some embodiments, the anastomosis device 200 can be formed in a manner such that the elongate member defines a flange cell 228 of the first apposition portion 202, the elongate member traverses the central portion 206, the elongate member defines a flange cell 228 of the second apposition portion 204, the elongate member traverses the central portion 206, and thereafter the elongate member repeats the pattern to form additional flange cells while traversing the central portion 206 in between. In some embodiments, each successive pattern and each successive flange cell 228 can be out of phase with those directly preceding.

The central portion 206 is shown in a deployed or expanded configuration in FIGS. 2A-2C. In some embodiments, the central portion 206, as described above, can include a variety of metallic shape memory materials and super-elastic alloys. Thus, the central portion 206 can be configured to self-expand to the deployed configuration. In some embodiments, the central portion 206 is balloon expandable into the deployed configuration. Alternatively, supplemental expansion forces can be applied to a self-expandable device by balloon dilation. The diameter of the central portion 206 can be made in any size as desired in order to suit the intended use and/or delivery system of the anastomosis device 200. For example, in the low-profile delivery configuration the anastomosis device 200 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. When the anastomosis device 200 is configured in its expanded deployed configuration as shown, the diameter of the central portion 206 increases to a deployed diameter. In some implementations, the deployed outer diameter of the central portion 206 is configured to at least partially anchor the device 200 via an interference fit with the tissue aperture in which the central portion 206 resides. Additionally, when the central portion 206 and the tissue aperture have an interference fit relationship, para-device leakage may be reduced or minimized. In such a case, leakage of the contents of the organs, conduits, and other types of tissue structures in which the anastomosis device 200 may be deployed can be substantially prevented. For example, when the anastomosis device 200 is used between a gallbladder and GI tract (e.g., refer to FIG. 1), leakage into the abdominal cavity can be substantially prevented.

In some implementations, the deployed outer diameter of the central portion 206 is slightly less than the diameter of the tissue aperture in which the central portion 206 resides, and the apposition portions 202 and 204 compress the tissue to provide the migration resistance. In some embodiments, the fully expanded diameter of the central portion 206 is about 30 mm, or about 25 mm, or about 20 mm, or about 15 mm, or about 12 mm, or about 10 mm, or about 8 mm, or about 6 mm, or about 4 mm, and the like.

In some embodiments, one or more portions of the anastomosis device 200 includes a covering material. For enhanced visualization of the framework of the anastomosis device 200, the anastomosis device 200 is shown in FIGS. 2A-2E without a covering material. In some embodiments, a covering material is disposed on at least some portions (or on all) of the first apposition portion 202, the second apposition portion 204, and/or the central portion 206. In some embodiments, some portions of the first apposition portion 202, the second apposition portion 204, and/or the central portion 206 are not covered by the covering material.

In some embodiments, the covering material is generally fluid impermeable. That is, in some embodiments the covering material is made of a material that inhibits or reduces passage of blood, bile and/or other bodily fluids and materials through the covering material itself. In some embodiments, the covering material has a material composition and configuration that inhibits or prevents tissue ingrowth and/or endothelialization or epithelialization into the covering material. Some such embodiments that are configured to inhibit or prevent tissue ingrowth and/or endothelialization can be more readily removed from the patient at a future date if so desired. In some embodiments, the covering material, or portions thereof, has a microporous structure that provides a tissue ingrowth scaffold for durable sealing and/or supplemental anchoring strength of the anastomosis device 200.

In some embodiments, the covering material comprises a fluoropolymer, such as an expanded polytetrafluoroethylene (ePTFE) polymer, or polyvinylidene fluoride (PVDF). In some embodiments, the covering material comprises a polyester, a silicone, a urethane, another biocompatible polymer, polyethylene terephthalate (e.g., Dacron®), bioabsorbable materials, copolymers, or combinations thereof. In some embodiments, the covering material comprises a bioabsorbable web. In some other embodiments, the bioabsorbable material may also provide an anti-migration feature by promoting attachment between the device 200 and tissue until the bioabsorbable material is absorbed.

In some embodiments, the covering material (or portions thereof) is modified by one or more chemical or physical processes that enhance one or more properties of the material. For example, in some embodiments, a hydrophilic coating is applied to the covering material to improve the wettability and echo translucency of the material. In some embodiments, the covering material, or portions thereof, is modified with chemical moieties that facilitate one or more of endothelial cell attachment, endothelial cell migration, endothelial cell proliferation, and resistance to or promotion of thrombosis. In some embodiments, the covering material, or portions thereof, is modified to resist biofouling. In some embodiments, the covering material, or portions thereof, is modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments, the drug substance is a corticosteroid, a human growth factor, an anti-mitotic agent, an antithrombotic agent, a stem cell material, or dexamethasone sodium phosphate, to name some embodiments. In some embodiments, a pharmacological agent is delivered separately from the covering material to the target site to promote tissue healing or tissue growth.

Coatings and treatments may be applied to the covering material before or after the covering material is joined or disposed on the framework of the anastomosis device 200. Additionally, one or both sides of the covering material, or portions thereof, may be coated. In some embodiments, certain coatings and/or treatments are applied to the covering material(s) located on some portions of the anastomosis device 200, and other coatings and/or treatments are applied to the material(s) located on other portions of the anastomosis device 200. In some embodiments, a combination of multiple coatings and/or treatments are applied to the covering material, or portions thereof. In some embodiments, certain portions of the covering material are left uncoated and/or untreated. In some embodiments, the device 200 is fully or partially coated to facilitate or frustrate a biological reaction, such as, but not limited to, endothelial cell attachment, endothelial cell migration, endothelial cell proliferation, and resistance to or promotion of thrombosis.

In some embodiments, a first portion of the covering material is formed of a first material and a second portion of the covering material is formed of a second material that is different than the first material. In some embodiments, the covering material includes multiple layers of materials, which may be the same or different materials. In some embodiments, portions of the covering material have one or more radiopaque markers attached thereto to enhance in vivo radiographic visualization of the anastomosis device 200, or one or more echogenic areas to enhance ultrasonic visibility.

In some embodiments, one or more portions of the covering material are attached to the framework of the device 200, such as the central portion 206 and/or the apposition portions 202 and 204. The attachment can be accomplished by a variety of techniques such as, but not limited to, stitching the covering material to the framework of the device 200, adhering the covering material to the framework of the device 200, laminating multiple layers of the covering material to encompass portions of the elongate members of the device 200, using clips or barbs, or laminating multiple layers of the covering material together through openings in the framework of the device 200. In some embodiments, the covering material is attached to the framework of the device 200 at a series of discrete locations thereby facilitating the flexibility of the framework. In some embodiments, the covering material is loosely attached to the framework of the device 200. It is to be appreciated that the covering material may be attached to the framework of the device 200 using other techniques or combinations of techniques described herein.

In some embodiments, the framework of the device 200 (or portions thereof) is coated with a bonding agent (e.g., fluorinated ethylene propylene or other suitable adhesive) to facilitate attachment of the covering material to the framework. Such adhesives may be applied to the framework using contact coating, powder coating, dip coating, spray coating, or any other appropriate means.

The covering material can adapt to changes in the length and/or diameter of the central portion 206 in a variety of manners. In a first example, the covering material can be elastic such that the covering material can stretch to accommodate changes in the length and/or diameter of the device 200. In a second example, the covering material can include slackened material in the low-profile delivery configuration that becomes less slackened or totally unslackened when the device 200 is in the expanded configuration. In a third example, the covering material can include folded portions (e.g., pleats) that are folded in the low-profile configuration and less folded or totally unfolded when the device 200 is in the expanded configuration. In other embodiments, an axial adjustment member is free of covering material. In some embodiments, combinations of such techniques, and/or other techniques can be used whereby the covering material can adapt to changes in the length and/or diameter of the central portion 206.

Figure 3A:
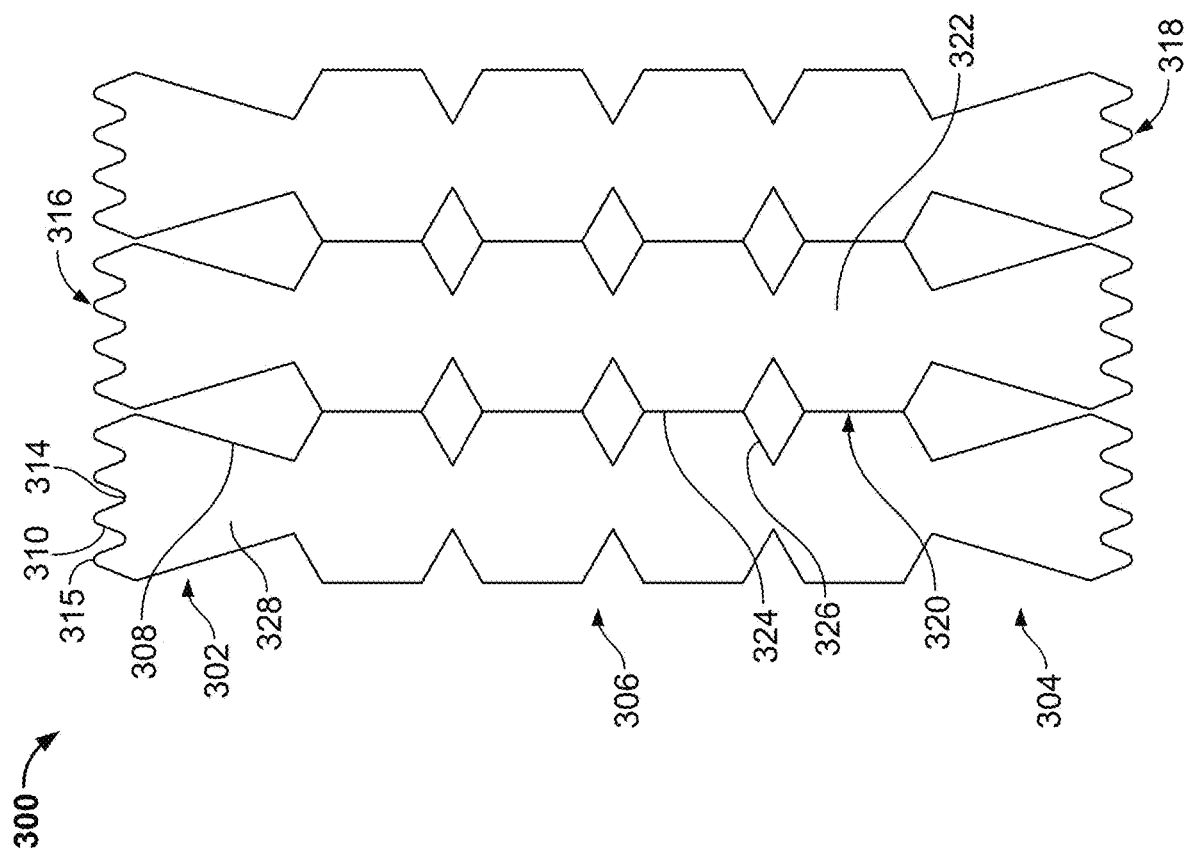
FIG. 3A is a flat pattern of an anastomosis device in accordance with some embodiments.

FIG. 3A is a flat pattern of an anastomosis device 300 in accordance with some exemplary embodiments. In some embodiments, the anastomosis device 300 can be similar to the anastomosis device 200 described above. For example, the anastomosis device 300 includes a framework of elongate elements that defines a first apposition portion 302, a second apposition portion 304, and a central portion 306. The central portion 306 is disposed between and interconnects the first apposition portion 302 and the second apposition portion 304. In some embodiments, the anastomosis device 300 is formed from a tubular material that is cut (e.g., laser cut) and shape-set to a preferred form. Other materials and fabrication techniques are also envisioned. A covering material as described above (not shown in FIG. 3A) can be disposed on at least some portions (or all) of the framework of the anastomosis device 300.

The anastomosis device 300 is shown in FIG. 3A as a flat pattern for clarity. However, the anastomosis device 300 can be formed into a tubular shape, with the central portion 306 forming a substantially cylindrical structure, and with the first and second apposition portions 302 and 304 extending outward from opposing ends of the central portion 306. In some embodiments, the central portion 306 can form a tubular body that defines a lumen that extends between the first apposition portion 302 and the second apposition portion 304. The first and second apposition portions 302 and 304 can form flanges extending substantially radially outward from opposite ends of the central portion 306. In some implementations, the lumen defined by the central portion 306 provides an anastomosis passageway or tunnel through which biological materials and liquids can pass. It should be understood that when the anastomosis device 300 is implanted in a patient, the configuration of the device 300 may be somewhat different than shown because of the external forces from the patient's anatomy that are exerted on the device 300.

In some embodiments, the connecting members 310 combine to form circumferential rings 316 and 318 extending substantially circumferentially around a radially-outer circumference of each of the first and second apposition portions 302 and 304, respectively. The circumferential rings 316 and 318 can have a shape that is wavy or that undulates circumferentially around the outer edges of the first and second apposition portions 302 and 304. In some embodiments, the circumferential rings 316 and 318 can undulate sinusoidally around the edges of one or both of the first and second apposition portions 302 and 304. Forming one or both of the circumferential rings 316 and 318 with a sinusoidal, serpentine, or otherwise undulating shape can increase an amount of surface area of contact between the first and second apposition portions 302 and 304 and tissue, thus reducing force at a given location on that tissue. Forming one or both of the circumferential rings 316 and 318 with a sinusoidal, serpentine, or otherwise undulating shape can also help facilitate crushability (for deployment via a low-profile) of the first and second apposition portions 302 and 304 while maintaining other desirable properties.

The central portion 306 can include a series of body struts 320, each extending substantially axially and forming the central body of the anastomosis device 300. The body struts 320 define body cells 322 of the central portion 306 and separate the respective body cells 322 from circumferentially-adjacent body cells 322. In some embodiments, each of the body struts 320 can include a plurality of axially-extending portions 324 interconnected with a plurality of angled portions 326. This can allow the body struts 320 to create a relatively strong central portion 306 without necessarily interconnecting the body struts 320 across the body cells 322 at several locations along the length of the body struts 320.

The struts 308 of the apposition portions 302 and 304 can define flange cells 328 between the struts 308. In some embodiments, the flange cells 328 are open cells (with no strut separating the flange cells 328 from the central portion 306). In some embodiments, the flange cells 328 are closed at a distal-most end of the flange cells 328 by connecting members 310 and are open at a center-most end of the flange cells 328, such that the flange cells 328 are open to the body cells 322. The angled portions 326 can partially separate axially-adjacent body cells 322 but leave gaps such that each body cells 322 is open to each axially-adjacent body cell 322.

Figure 3D:
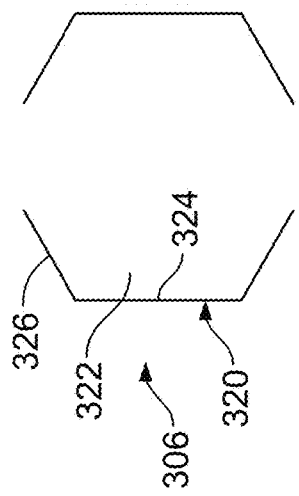
FIG. 3D is an enlarged view of a cell of the anastomosis device of FIG. 3A in a deployed configuration.
Figure 3E:
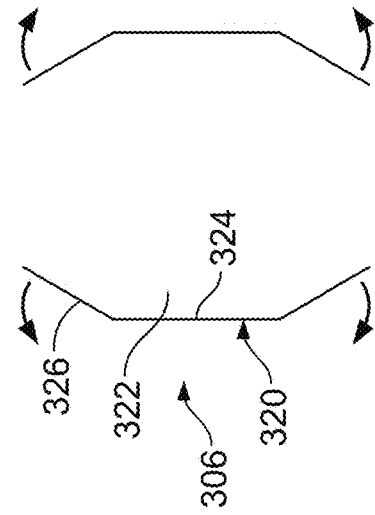
FIG. 3E is an enlarged view of a cell of the anastomosis device of FIG. 3A in a crushed configuration.
Figure 3B:
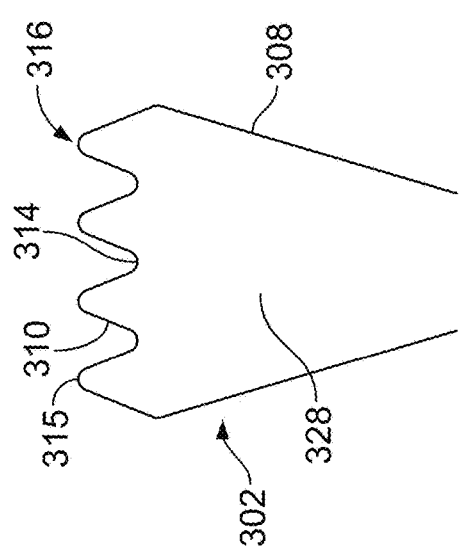
FIG. 3B is an enlarged view of a flange cell of the anastomosis device of FIG. 3A in a deployed configuration.
Figure 3C:
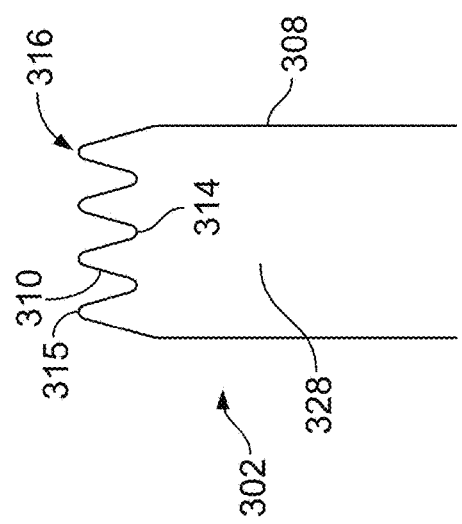
FIG. 3C is an enlarged view of the flange cell of the anastomosis device of FIG. 3A in a low-profile delivery configuration.

FIG. 3B is an enlarged view of a single flange cell 328 of the anastomosis device 300 in a deployed configuration. FIG. 3C is an enlarged view of a single flange cell 328 of the anastomosis device 300 in a crushed configuration. The anastomosis device 300 can be elastically crushed, folded, and/or collapsed into a low-profile delivery configuration (with the flange cell 328 in the crushed configuration illustrated in FIG. 3C) for containment within a lumen for transcatheter or endoscopic/thorascopic delivery lumen. In some embodiments, the anastomosis device self-expands (upon deployment from the delivery lumen) to an operative size and configuration once positioned at a desired target site within a body (e.g., the flange cell 328 expands to the deployed configuration as illustrated in FIG. 3B).

FIG. 3D is an enlarged view of the body cell 322 of the anastomosis device 300 in a deployed configuration. FIG. 3E is an enlarged view of the body cell 322 of the anastomosis device 300 in a crushed configuration.

The frame of the anastomosis device 300 can be formed using any of the materials and techniques described herein. For example, in some embodiments the frame of the anastomosis device 300 is formed from a precursor material that is cut to create the framework. In some such embodiments, the precursor material is a single piece of precursor material such as, but not limited to, a tubular material or a sheet material. In some embodiments, the frame of the anastomosis device 300 can be formed as a wire-wound structure of a single wire or a plurality of wires that form the structures of the first apposition portion 302, the second apposition portion 304, and the central portion 306, so as to create the open structures of the body cells 322 and the flange cells 328 as well as the undulating shape of the circumferential rings 316 and 318. In some embodiments, a wire-wound structure may advantageously facilitate functionality of the open structures of the body cells 322 and the flange cells 328 as well the undulating shape of the circumferential rings 316 and 318.

In some embodiments, the anastomosis device 300 can be wire-wound (or laser cut) in a manner such that an elongate member forms (i) a first pattern traversing the central portion 306 along a longitudinal axis, (ii) a first flange cell 328 of the first apposition portion 302, (iii) a second pattern traversing the central portion 306 along the longitudinal axis opposing the first pattern, (iv) a second opposing flange cell 328, and so on. The elongate member can be formed to repeat those patterns of the central portion 306 and flanges cells 328 to construct a complete anastomosis device 300.

In some embodiments, the anastomosis device 300 can be wire-wound (or laser cut) in a manner such that the elongate member defines a flange cell 328 of the first apposition portion 302, the elongate member traverses the central portion 306, the elongate member defines a flange cell 328 of the second apposition portion 304, the elongate member traverses the central portion 306, and thereafter the elongate member repeats the pattern to form additional flange cells while traversing the central portion 306 in between. In some such embodiments, each successive pattern and flange cell are symmetric to those proceeding.

FIG. 4 is a flat pattern of an anastomosis device 400 in accordance with other exemplary embodiments. In some embodiments, the anastomosis device 400 can be similar to the anastomosis devices 200 and 300 described above. For example, in some embodiments the anastomosis device 400 includes a framework of elongate elements that defines a first apposition portion 402, a second apposition portion 404, and a central portion 406. The central portion 406 is disposed between and interconnects the first apposition portion 402 and the second apposition portion 404. A covering material as described above (not shown in FIG. 4) can be disposed on at least some portions (or all) of the framework.

The anastomosis device 400 is shown in FIG. 4 as a flat pattern for clarity. However, the anastomosis device 400 can be formed into a tubular form, with the central portion 406 forming a substantially cylindrical structure, and with the first and second apposition portions 402 and 404 extending outward from opposing ends of the central portion 406. In some embodiments, the central portion 406 can form a tubular body that defines a lumen that extends between the first apposition portion 402 and the second apposition portion 404. The first and second apposition portions 402 and 404 can form flanges extending substantially radially outward from opposite ends of the central portion 406. In some implementations, the lumen defined by the central portion 406 provides an anastomosis passageway or tunnel through which biological materials can pass. It should be understood that when the anastomosis device 400 is implanted in a patient, the configuration of the device 400 may be somewhat different than shown because of the external forces from the patient's anatomy that are exerted on the device 400.

In some embodiments, the connecting members 410 combine to form circumferential rings 416 and 418 extending substantially circumferentially around a radially-outer circumference of each of the first and second apposition portions 402 and 404, respectively. The circumferential rings 416 and 418 can have a shape that is wavy or that undulates circumferentially around edges of the first and second apposition portions 402 and 404. In some embodiments, the circumferential rings 416 and 418 can have a shape that undulates, as can be seen in FIG. 4. In some embodiments, the circumferential rings 416 and 418 can undulate sinusoidally along the edges of one or both of the first and second apposition portions 402 and 404. Forming one or both of the circumferential rings 416 and 418 with a sinusoidal, serpentine, or otherwise undulating shape can, in some implementations, increase an amount of surface area of contact between the first and second apposition portions 402 and 404 and tissue, thus reducing the force at a given location on that tissue. Forming one or both of the circumferential rings 416 and 418 with a sinusoidal, serpentine, or otherwise undulating shape can also help facilitate crushability of the first and second apposition portions 402 and 404 while maintaining other desirable properties.

The central portion 406 can include a series of body struts 420, each body strut extending substantially axially and forming the central body of the anastomosis device 400. The body struts 420 define body cells 422 of the central portion 406 and separate the respective body cells 422 from circumferentially-adjacent body cells 422. In some embodiments, each of the body struts 420 may include a plurality of axially-extending portions 424 interconnected with a plurality of angled portions 426. Such a configuration can allow the body struts 420 to create a relatively strong central portion 406 without necessarily interconnecting the body struts 420 at several locations along the length of the body struts 420.

In some embodiments, the struts 408 of the apposition portions 402 and 404 can define flange cells 428 between the struts 408. In some such embodiments, the flange cells 428 can be open cells, with no strut separating the flange cells 428 from the central portion 406. The flange cells 428 can be closed at a distal-most end of the flange cells 428 by connecting members 410 and can be open at a center-most end of the flange cells 428, such that the flange cells 428 can be open to the body cells 422. As illustrated in FIG. 4, the flange cells 428 of the first apposition portion 402 are aligned with the body cells 422 and open to the body cells 422, and the flange cells 428 of the second apposition portion 404 are aligned with the body struts 420 but are askew of the body cells 422.

In some embodiments, the angled portions 426 can partially separate longitudinally-adjacent body cells 422 but leave gaps such that each of the body cells 422 is open to each longitudinally-adjacent body cell 422.

In some embodiments, the anastomosis device 400 can be wire-wound (or laser cut) in a manner such that an elongate member forms (i) a first pattern traversing the central portion 406 along a longitudinal axis, (ii) a first flange cell 428 of the first apposition portion 402, (iii) a second pattern traversing the central portion 406 along the longitudinal axis opposing the first pattern, (iv) a second opposing flange cell 428, and so on. The elongate member can repeat those patterns to form all of the central portion 406 and flanges cells 428 of the anastomosis device 400.

In other embodiments, the anastomosis device 400 can be wire-wound (or laser cut) in a manner such that the elongate member defines a flange cell 428 of the first apposition portion 402, the elongate member traverses the central portion 406, the elongate member defines a flange cell 428 of the second apposition portion 404, the elongate member traverses the central portion 406, and thereafter the elongate member repeats the pattern to form additional flange cells while traversing the central portion 406 in between. In some embodiments, each successive pattern and each successive flange cell 428 can be out of phase with those proceeding. In some embodiments, each successive pattern and each successive flange cell 428 can be in phase with those proceeding.

FIG. 5 is a flat pattern of an anastomosis device 500 in accordance with some exemplary embodiments. In some embodiments, the anastomosis device 500 can be similar to the anastomosis devices 200, 300, and 400 described above. For example, the anastomosis device 500 includes a framework of elongate elements that defines a first apposition portion 502, a second apposition portion 504, and a central portion 506. The central portion 506 is disposed between and interconnects the first apposition portion 502 and the second apposition portion 504. A covering material as described above (not shown in FIG. 5) can be disposed on at least some portions (or on all portions) of the framework.

The anastomosis device 500 is shown in FIG. 5 as a flat pattern for clarity. However, the anastomosis device 500 can be formed into a tubular form, with the central portion 506 forming a substantially cylindrical structure, and with the first and second apposition portions 502 and 504 extending outward from opposing ends of the central portion 506. In some embodiments, the central portion 506 can form a tubular body that defines a lumen that extends between the first apposition portion 502 and the second apposition portion 504. The first and second apposition portions 502 and 504 can form flanges extending substantially radially outward from opposite ends of the central portion 506. In some implementations, the lumen defined by the central portion 506 provides an anastomosis passageway or tunnel through which biological materials can pass. It should be understood that when the anastomosis device 500 is implanted in a patient, the configuration of the device 500 may be somewhat different than shown because of the external forces from the patient's anatomy that are exerted on the device 500.

In some embodiments, the connecting members 510 combine to form circumferential rings 516 and 518 extending substantially circumferentially around a radially-outer circumference of each of the first and second apposition portions 502 and 504, respectively. The circumferential rings 516 and 518 can have a shape that is wavy or that undulates circumferentially around edges of the first and second apposition portions 502 and 504. In some embodiments, the circumferential rings 516 and 518 can have a shape that undulates, as shown in FIG. 5. In some such embodiments, the circumferential rings 516 and 518 can undulate sinusoidally along the edges of one or both of the first and second apposition portions 502 and 504. Forming one or both of the circumferential rings 516 and 518 with a sinusoidal, serpentine, or otherwise undulating shape may, in some implementations, increase an amount of surface area of contact between the first and second apposition portions 502 and 504 and tissue, thus reducing force at a given location on that tissue. Forming one or both of the circumferential rings 516 and 518 with a sinusoidal, serpentine, or otherwise undulating shape can also help facilitate crushability to a low-profile delivery configuration of the first and second apposition portions 502 and 504 while maintaining other desirable properties.

The central portion 506 can include a series of body struts 520, each body strut extending substantially axially and forming the central body of the anastomosis device 500. In some embodiments, the body struts 520 define body cells 522 of the central portion 506 and separate the respective body cells 522 from circumferentially-adjacent body cells 522. In some embodiments, each of the body struts 520 can include a plurality of axially-extending portions 524 interconnected with a plurality of angled portions 526. This can allow the body struts 520 to create a relatively strong central portion 506 without necessarily interconnecting the body struts 520 at several locations along the length of the body struts 520. The struts 508 of the apposition portions 502 and 504 can define flange cells 528 between the struts 508.

As illustrated in FIG. 5, in some embodiments each column of body cells 522 is aligned with a flange cell 528 at one end, and is open at an opposite end. In some embodiments, the body cells 522 can be axially aligned with and open to a gap 530 extending between adjacent struts 508 of one or both of the first and second apposition portions 502 and 504. The angled portions 526 can partially separate axially-adjacent body cells 522 but can leave gaps such that each body cells 522 is open to each axially-adjacent body cell 522.

In some embodiments, the anastomosis device 500 can be formed in a manner such that an elongate member forms (i) a first pattern traversing the central portion 506 along a longitudinal axis, (ii) a first flange cell 528 of the first apposition portion 502, (iii) a second pattern traversing the central portion 506 opposing the first pattern, (iv) a second opposing flange cell 528, and so on. In some embodiments, the elongate member repeats those patterns to form additional portions of the central portion 506 and flanges cells 528 to complete the anastomosis device 500.

In some embodiments, the anastomosis device 500 can be formed in a manner such that the elongate member defines a flange cell 528 of the first apposition portion 502, the elongate member traverses the central portion 506, the elongate member defines a flange cell 528 of the second apposition portion 504, the elongate member traverses the central portion 506, and thereafter the elongate member repeats the pattern to form additional flange cells while traversing the central portion 506 in between. In some embodiments, each successive pattern and each successive flange cell can be out of phase with those directly preceding. In some embodiments, each successive pattern and each successive flange cell can be in phase with those directly preceding.

Figure 6A:
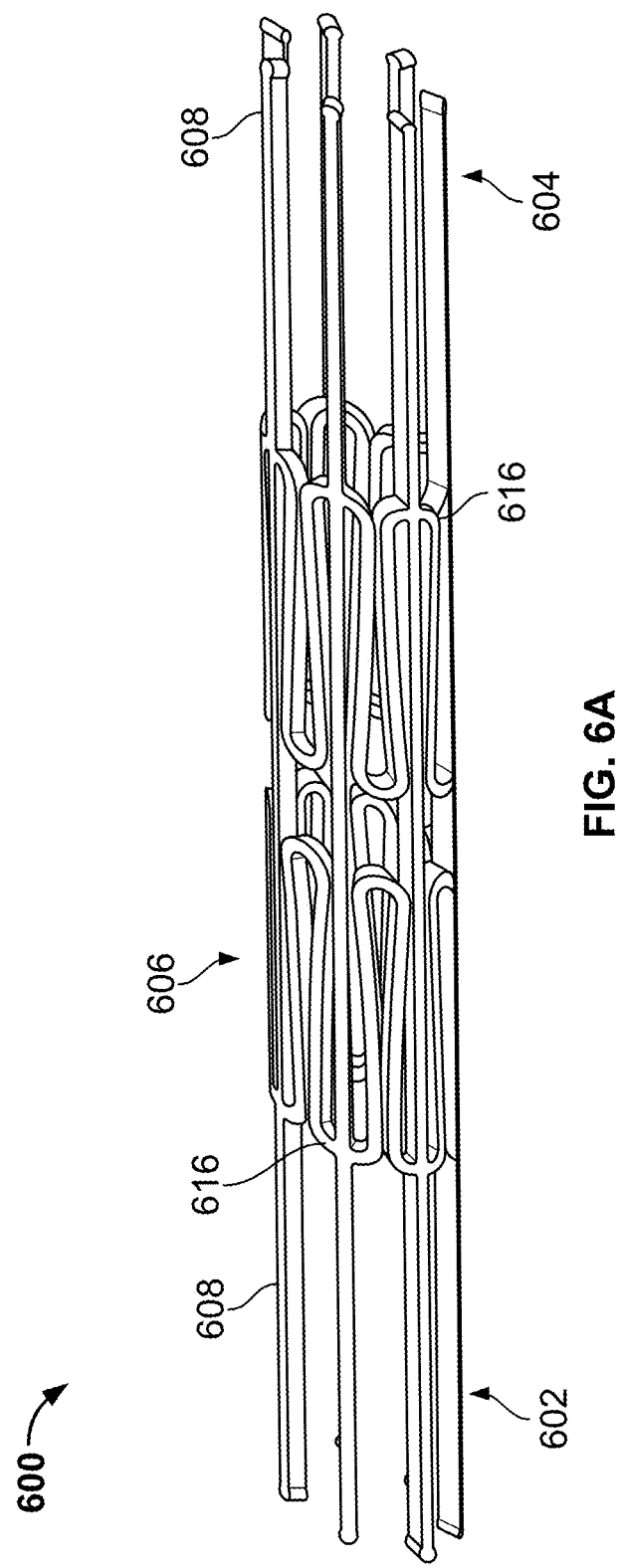
FIG. 6A is a perspective view of a framework of another exemplary anastomosis device in a low-profile delivery configuration in accordance with some embodiments.
Figure 6B:
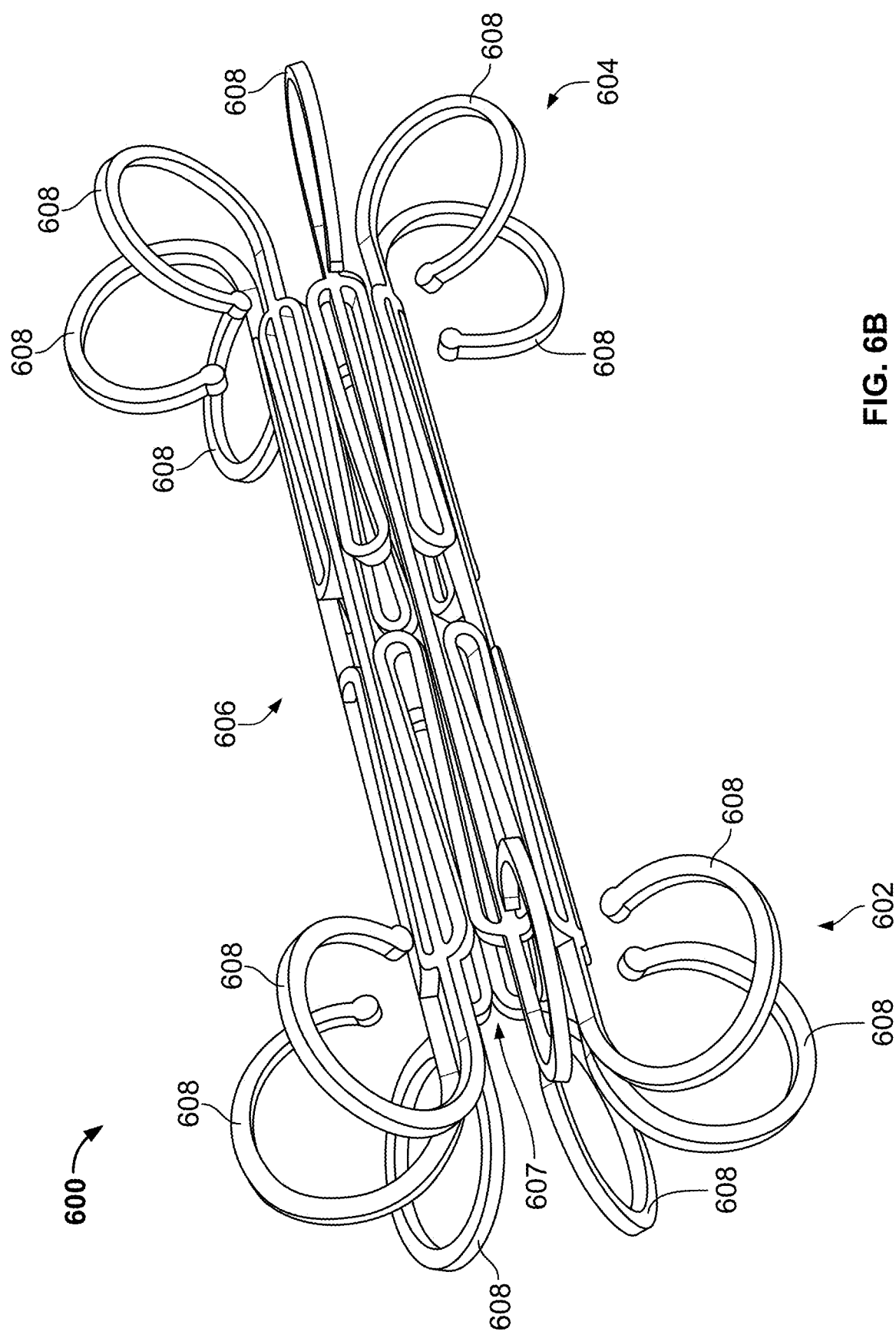
FIG. 6B is a perspective view of the framework of FIG. 6A in accordance with some embodiments.

Referring to FIGS. 6A and 6B, the framework 600 of another example anastomosis device includes a first apposition portion 602, a second apposition portion 604, and a central portion 606. For enhanced visualization of the framework 600, the framework 600 is shown without a covering material, however covering material(s) as described elsewhere herein can be applied. In FIG. 6A, the framework 600 is shown in a low-profile delivery configuration. In FIG. 6B, the apposition portions 602 and 604 are shown in their expanded (deployed) configurations, while the central portion 606 is still shown in its low-profile configuration. When the framework 600 is fully expanded, the central portion 606 will become radially enlarged (e.g., refer to FIGS. 7A-C).

The central portion 606 is disposed between the first apposition portion 602 and the second apposition portion 604. The central portion 606 defines a lumen 607 that extends between the first apposition portion 602 and the second apposition portion 604. In some embodiments, the lumen 607 provides an anastomosis passageway or tunnel through which biological materials and liquids can pass.

The materials, configurations, and techniques for construction of the framework 600 (and for the anastomosis devices that utilize framework 600) can be the same as those described above in reference to the anastomosis device 200 The first apposition portion 602 and the second apposition portion 604 are configured to engage one or more layers of tissue therebetween, and to provide apposition forces against the tissue surfaces. The apposition forces provided by the first and second apposition portions 602 and 604 can facilitate attachment of the framework 600 to the tissue and provide displacement resistance such that the framework 600 can reliably remain positioned at a target site in a patient as desired.

The first and second apposition portions 602 and 604 are formed of elongate elements in the form of struts 608. In some embodiments, the struts 608 are configured to naturally form loops or semi-circles after deployment from a delivery sheath. In some such embodiments, the deployed apposition portions 602 and 604 are therefore comprised of a plurality of struts that jointly form toroid-shaped portions that are configured to contact tissue surfaces. In some embodiments, the deployed apposition portions 602 and 604 form other shapes such as, but not limited to, flanges, petals, hemispherical, and the like.

In the low-profile delivery configuration, the plurality of struts 608 are compressed such that they extend substantially parallel to the central portion 606. The materials of device 600 allow the anastomosis devices to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen.

The central portion 606 includes at least one stent ring 616. As shown, the stent rings 616 are aligned with each other along the longitudinal axis of the central portion 606. In some embodiments, the stent rings 616 exhibit a serpentine pattern. It is to be appreciated that suitable patterns for the devices described herein include a variety of shapes and/or patterns. In some embodiments, the stent rings 616 are interconnected to each other by at least one strut 608 of the apposition portions 602 and 604.

The central portion 606 is shown in a low-profile configuration. In some embodiments, the central portion 606, as discussed above, can include a variety of metallic shape memory materials and super-elastic alloys. Thus, the central portion 606 can be configured to self-expand to a deployed configuration. In some embodiments, the central portion 606 is balloon expandable to a deployed configuration. The diameter of the central portion 606 can be made in any size as desired in order to suit the intended use and/or delivery system of the anastomosis device. For example, the undeployed or low-profile delivery of the central portion 606 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. During deployment, the diameter of the central portion 606 adjusts to a deployment diameter. In some embodiments, the deployed diameter of the central portion 606 is configured to at least partially anchor the device 600 via an interference fit with a tissue aperture. In other embodiments, a distance between the apposition portions is configured at least partially to anchor the device 600. In some embodiments, the diameter of the central portion 606 increases, e.g., to about 30 mm, about 25 mm, about 20 mm, about 15 mm, about 12 mm, about 10 mm, about 8 mm, about 6 mm, about 4 mm, and the like.

Figure 7A:
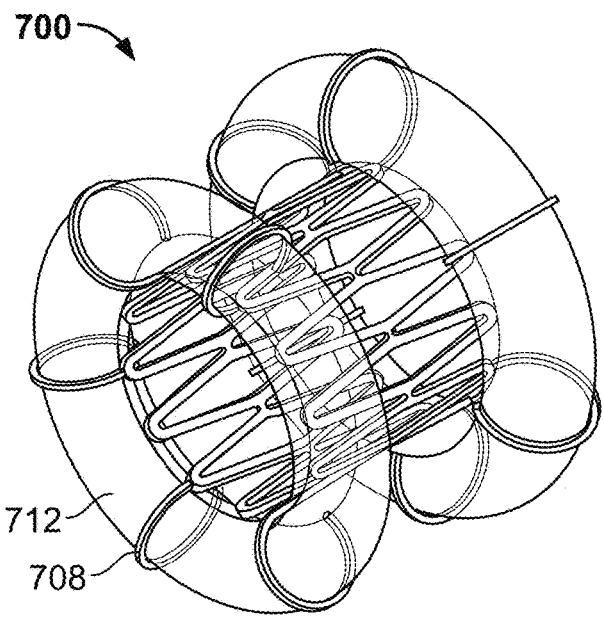
FIG. 7A is a perspective view of another exemplary anastomosis device in accordance with some embodiments.
Figure 7B:
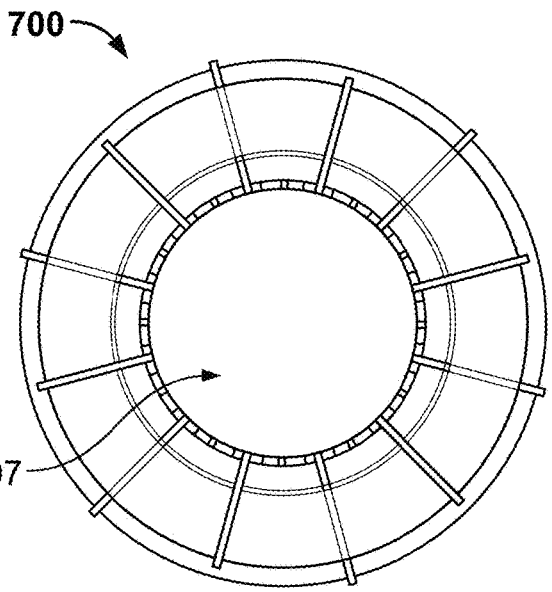
FIG. 7B is an end view of the anastomosis device of FIG. 7A.
Figure 7C:
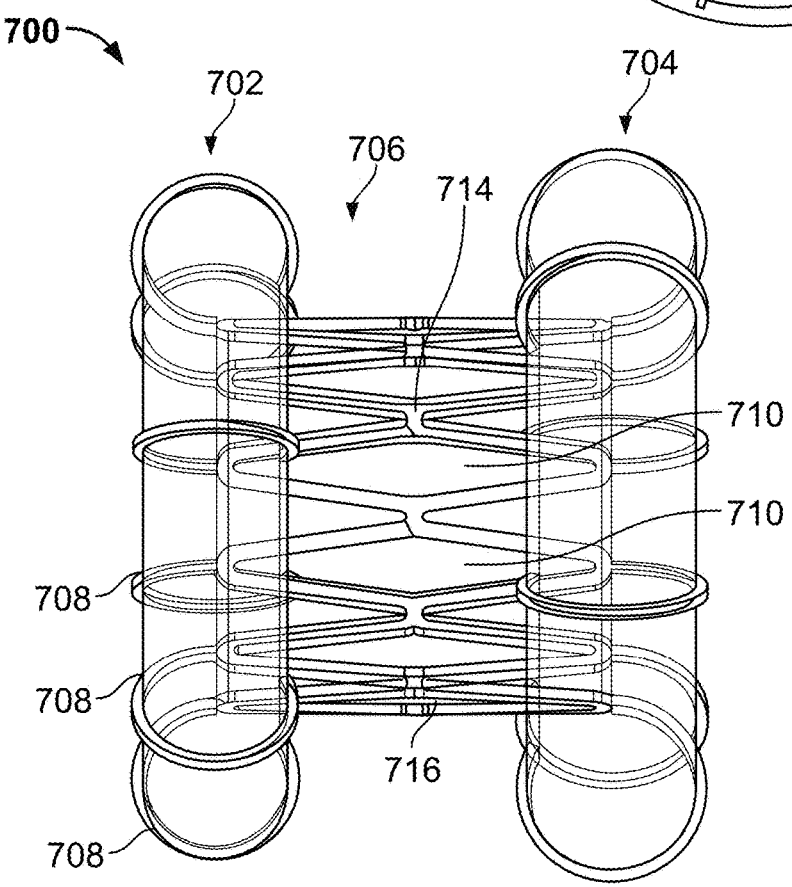
FIG. 7C is a side view of the anastomosis device of FIG. 7A.

Referring to FIGS. 7A-7C, another example anastomosis device 700 includes a framework of elongate elements that defines a first apposition portion 702, a second apposition portion 704, and a central portion 706. The central portion 706 is disposed between and interconnects the first apposition portion 702 and the second apposition portion 704. A covering material 712 is disposed on at least some portions of the framework. In some embodiments, the central portion 706 defines a lumen 707 that extends between the first apposition portion 702 and the second apposition portion 704. In some implementations, the lumen 707 provides an anastomosis passageway or tunnel through which biological materials or liquids can pass. The device 700 is shown in an expanded configuration. The expanded configuration is the configuration that the device 700 naturally exhibits in the absence of external forces acting upon the device 700. It should be understood that when the anastomosis device 700 is implanted in a patient, the configuration of the device 700 may be somewhat different than shown because of the external forces from the patient's anatomy that are exerted on the device 700.

The materials, configurations, and techniques for construction of the anastomosis device 700 can be the same as those described above in reference to the anastomosis device 200.

The apposition portions 702 and 704 of the anastomosis device 700 are analogous to the apposition portions 602 and 604 described above in reference to framework 600. The apposition portions 702 and 704 naturally configure themselves into the exemplary toroidal shapes shown.

In some embodiments, the central portion 706 is a cellular construction made up of multiple diamond-shaped cells 716 that are interconnected by joints 714. In other exemplary embodiments, such cells of the central portion 706 may have other shapes. In some embodiments, open spaces 710 are defined by the diamond-shaped cells 716. It should be understood that the depicted configuration of the central portion 706 is just one example, and many other types of configurations can be incorporated.

Figure 8A:
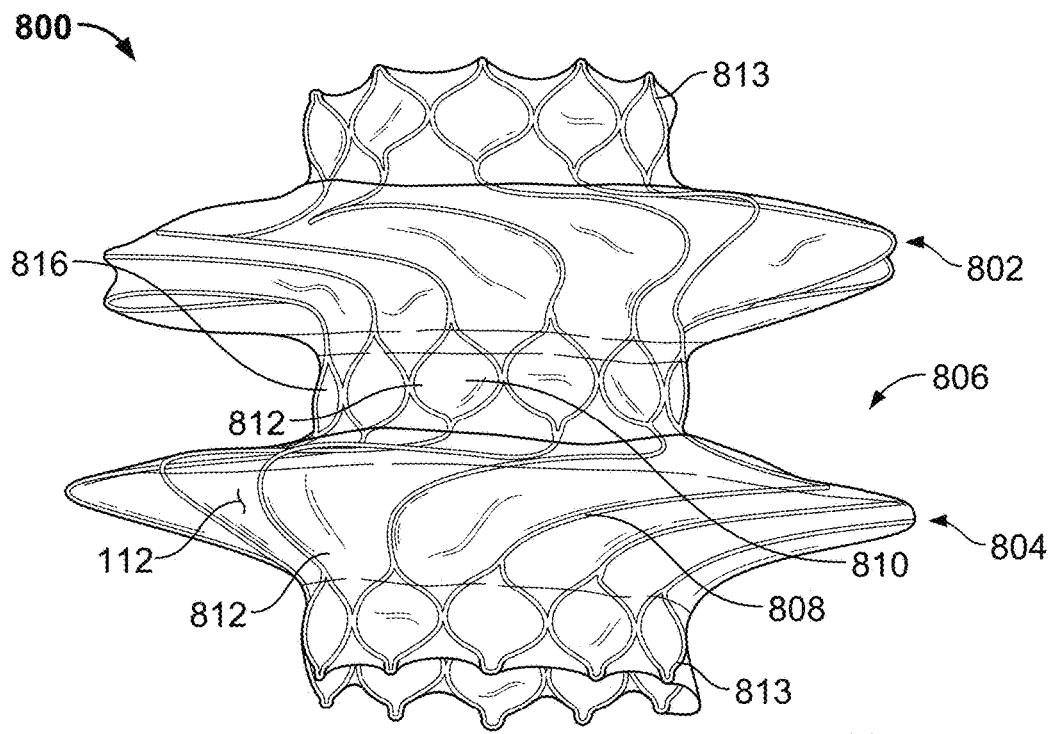
FIG. 8A is a perspective view of another exemplary anastomosis device in accordance with some embodiments.
Figure 8B:
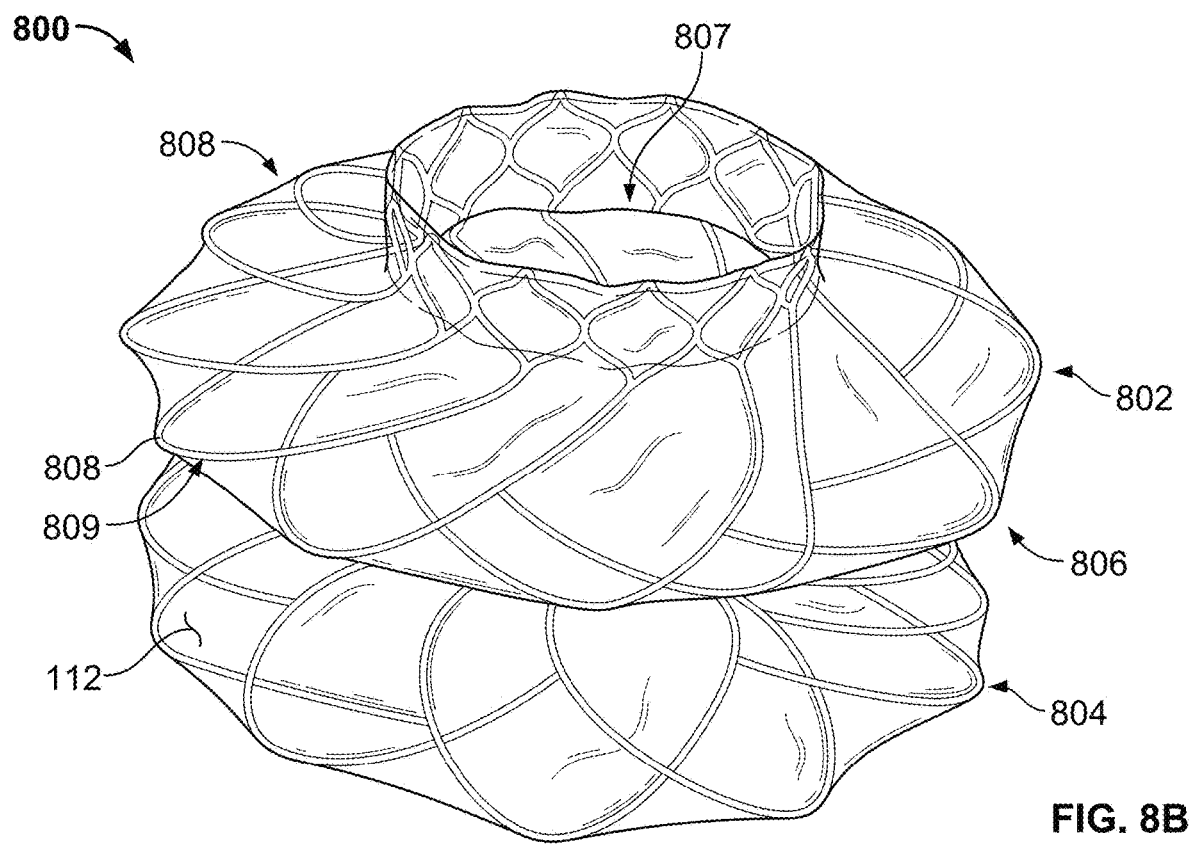
FIG. 8B is a different perspective view of the stent of FIG. 8A.

Referring to FIGS. 8A and 8B, an anastomosis device 800 includes a first apposition portion 802, a second apposition portion 804, and a central portion 806. The device 800 is shown with a covering material 112 (as per any of the other covering materials described herein, and attached to the device 800 in any of the manners described above). In some embodiments, the covering material 112 is attached to device 800 to create a single conduit 807. In some embodiments, the central portion 806 is covered independently from the apposition portions 802 and/or 804 such that cover on the apposition portions are distinct from the covering material 112 that creates the central lumen 807. In other embodiments, the central portion 806 is covered (or partially covered), while the apposition portions 802 and 804 remain free of covering material 112.

The central portion 806 is disposed between and interconnects the first apposition portion 802 and the second apposition portion 804. In some embodiments, an additional central end portion 813 extends beyond one or both of the apposition portions 802 and 804. The central end portion 813 can extend from one or both of the apposition portions 802 and to any desired length. In some embodiments, no central end portions 813 are included. Having one or both of the central end portion 813 can help to facilitate device removal in some cases. For example, an endoscopic grasper can be used to grasp the central end portion 813 and remove the device 800.

The central portion 806 defines a lumen 807 that extends between the first apposition portion 802 and the second apposition portion 804. In some embodiments, the lumen 807 provides an anastomosis passageway or tunnel through which biological materials or liquids can pass. The device 800 is shown in a deployed (expanded) configuration. The expanded or deployed configuration is the configuration that the device 800 or a portion thereof naturally exhibits in the absence of external forces acting upon the device 800.

In some embodiments, the first apposition portion 802, the second apposition portion 804, and the central portion 806 can comprise a spring wire (e.g., L605 steel or stainless steels), shape memory alloy wire (e.g., nitinol or nitinol alloys), super-elastic alloy wire (e.g., nitinol or nitinol alloys), other suitable types of wires, or combinations thereof. In some such embodiments, the first apposition portion 802, the second apposition portion 804, and the central portion 806 can be formed from the same piece of precursor material that is cut to create the wire structure as desired. For example, in some such embodiments the precursor material is a tube (e.g., a nitinol tube) that is laser cut to form the desired wire structure. In some embodiments, different types of wires are used at different locations of the first apposition portion 802, the second apposition portion 804, and/or the central portion 806. In other embodiments, the first apposition portion 802, the second apposition portion 804, and the central portion 806 or portions thereof may be constructed of polymeric materials.

The first apposition portion 802 and the second apposition portion 804 are configured to engage one or more layers of tissue therebetween, and to provide apposition forces against the tissue surfaces. The apposition forces provided by the first and second apposition portions 802 and 804 can facilitate fixation of the device 800 to the tissue and provide displacement resistance such that the device 800 can reliably remain positioned at a target site in a patient as desired. In the depicted embodiment, each of the first and second apposition portions 802 and 804 comprise a series of overlapping petals 809 that are collectively configured to form, in a general sense, discs that contact tissue surfaces. Although the discs shown in the depicted embodiment 800 are perpendicular to the central portion 806, the discs of first and second apposition portions 802 and 804 can be formed at non-orthogonal angles to facilitate apposition of varying tissue thicknesses and tissue topographies. The discs of first and second apposition portions 802 and 804 distribute the apposition pressure to a large tissue contact surface area, thereby facilitating apposition of diseased tissue (e.g. gangrenous) with minimal force.

In some embodiments, the first apposition portion 802 and the second apposition portion 804 each include a plurality of struts 808 that generally form a series of petals 809 having an S-shaped bend. These bends can affect the available apposition force and improve the ease of manufacturing. For example, during some manufacturing processes of device 800, the device pattern is cut from a cylindrical tube and the proximal end of the cut tube is compressed towards the distal end of the cut tube. Including an S-shaped bend in the device can be advantageous during this process. In other embodiments, increasing the number of the petals 809, the amount of overlap, and/or the thickness of the struts 808 can increase the available apposition force. In some embodiments, the first apposition portion 802 and/or the second apposition portion 804 can be formed in different manners (other than the series of petals 809 having an S-shaped bend). For example, in some embodiments the first apposition portion 802 and/or the second apposition portion 804 can be formed as loops that approximate radial spokes, and the like.

The number of petals 809 and the percentage of overlap of adjacent petals 809 can be selected to tailor the apposition force and area as desired. In some embodiments, each strut 808 is connected to one rhombus shaped cell on either end of the struts 808. In some such embodiments, the diameter of the first and second apposition portions 802 and 804 are determined by the length of the struts 808 that connects the cells and the angle of twist during manufacturing process. The S-shaped struts 808 establish a preferential bending location that can affect the shape of the petal 809 during shape setting process. In some embodiments, the S-shaped struts 808 can provide flexibility in design by not having to attach an entire length of frame to graft material and/or not having to use an elastomer material for graft. In some embodiments, the S-shaped struts 808 can permit attachment of relatively thin and flexible material for a relatively small device profile. In some embodiments, the S-shaped struts 808 can enable collapsibility of the first and second apposition portions 802 and 804, and ultimately improve the ability of the device 800 to be loaded within a sheath, and deployed via an endoscope working channel.

When the anastomosis device is configured in its low-profile delivery configuration, the plurality of struts 808 are compressed such that they extend substantially parallel to the longitudinal axis of the central portion 806. In some embodiments, the materials of device 800 allow the anastomosis devices to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen. In addition, the device 800 may exhibit, for example, beneficial fatigue resistance and elastic properties.

The central portion 806 includes at least one stent ring 816. As shown, the stent ring 816 includes a series of interconnected cells 810. During radial expansion, the cell 810 expands in the circumferential direction and collapses in the longitudinal direction. The radial strength of the central portion 806 can be increased by varying the geometry of the stent ring, varying the tube thickness of the initial tubular construct, or selecting a stronger material. It should be clear that suitable patterns for the devices described herein include a variety of different shapes and/or patterns. In some embodiments, the stent rings 816 are interconnected to each other by at least one bridge member 812.

The central portion 806 is shown in an expanded or deployed configuration. In some embodiments, the central portion 806, as discussed above, can include a variety of metallic shape memory materials and super-elastic alloys. Thus, the central portion 806 can be configured to self-expand to a deployed configuration. In some embodiments, the central portion 806 is balloon expandable to a deployed configuration. The diameter of the central portion 806 can be made in any size as desired in order to suit the intended use and/or delivery system of the anastomosis device. For example, the undeployed or low-profile delivery of the central portion 806 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. The device 800 can be longitudinally stretched to reduce the first and second apposition portions 802 and 804 to a smaller diameter. The size of the first and second apposition portions 802 and 804 can be reduced to at least as small as central portion 806 of the device 800. This reduction in size of the first and second apposition portions 802 and 804 enables crushing/crimping of the device 800 on to a catheter for endoscopic delivery, for example.

During deployment, the diameter of the central portion 806 expands to a larger diameter. In some embodiments, the deployed diameter of the central portion 806 is configured to at least partially anchor the device 800 via an interference fit with the tissue aperture. In some embodiments, the diameter of the central portion 806 increases, e.g., to about 30 mm, about 25 mm, about 20 mm, about 15 mm, about 12 mm, about 10 mm, about 8 mm, about 6 mm, about 4 mm, and the like.

In other embodiments, a distance between the apposition portions is configured at least partially to anchor the device 800. In some embodiments, the distance between the apposition portions is less than 5 mm, e.g., less than 4 mm, less than 3 mm, less than 2 mm, less than 1 mm, and so forth. In some embodiments, the distance between the flange member 809 and the flange member design can be tailored accommodate tissue conditions pre and post drainage. For example, the flanges 809 can be sufficiently flexible and the distance between the flanges sized so as to avoid pressure necrosis on the thicker tissue.

Referring to FIGS. 9A-9E, an anastomosis device 900 includes a first apposition portion 902, a second apposition portion 904, and a central portion 906 is illustrated. For simplicity, the device 900 is shown without a covering material; however, in some embodiments the covering material(s) described elsewhere herein can be applied to portions of or all or the frame material. The central portion 906 is disposed between the first apposition portion 902 and the second apposition portion 904. In some embodiments, the central portion 906 defines a lumen 907 that extends between the first apposition portion 902 and the second apposition portion 904. In some embodiments, the lumen 907 provides an anastomosis passageway or tunnel through which biological materials or liquids can pass. While in the depicted embodiment the central portion 906 includes a single row of cells, in some embodiments two, three, four, five, or more than five rows of cells are included. The device 900 is show in a deployed configuration. In some embodiments, the expanded or deployed configuration is the configuration that the device 900 or a portion thereof naturally exhibits in the absence of external forces acting upon the device 900.

In some embodiments, the first apposition portion 902, the second apposition portion 904, and the central portion 906 can comprise a spring wire (e.g., L605 steel or stainless steels), shape memory alloy wire (e.g., nitinol or nitinol alloys), super-elastic alloy wire (e.g., nitinol or nitinol alloys), other suitable types of wire, or combinations thereof. In some such embodiments, the first apposition portion 902, the second apposition portion 904, and the central portion 906 can be formed from the same piece of precursor material that is cut to create the wire structure as desired. For example, in some such embodiments the precursor material is a tube (e.g., a nitinol tube) that is laser cut to form the desired wire structure. In some embodiments, different types of wires are used at different locations of the first apposition portion 902, the second apposition portion 904, and/or the central portion 906. In some embodiments, the first apposition portion 902, the second apposition portion 904, and the central portion 906 or portions thereof may be constructed of polymeric materials.

The first apposition portion 902 and the second apposition portion 904 are configured to engage one or more layers of tissue therebetween, and to provide apposition forces against the tissue surfaces. The apposition forces provided by the first and second apposition portions 902 and 904 can facilitate attachment of the device 900 to the tissue and provide displacement resistance such that the device 900 can reliably remain positioned at a target site in a patient as desired. In some embodiments, each of the first and second apposition portions 902 and 904 are configured to form, in a general sense, discs that contact tissue surfaces.

The first apposition portion 902 and the second apposition portion 904 each include a plurality of struts 908. The anastomosis device 900 can be configured in a collapsed delivery configuration in which the plurality of struts 908 is compressed such that they extend substantially parallel to the central portion 906. The device 900 may exhibit, for example, beneficial fatigue resistance and elastic properties. In some embodiments, the materials of the device 900 allow the anastomosis devices to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen.

During deployment, the plurality of struts 908 protrude from the central portion 906 at an axial orientation and shape to achieve specific apposing pressures on the tissue. In some embodiments, the plurality of struts 908 protrude from the central portion 906 such the exposed face of the apposition portions 902 and 904 is substantially perpendicular to the longitudinal axis of the device 900.

Still referring to FIGS. 9A-9E, in the depicted embodiment the plurality of struts 908 are interconnected by a connecting member 910. The connecting member 910 is shown in a deployed configuration in which the connecting member 910 is arranged in a series of undulations each having a vertex 918 extending away from the central portion 906. When the anastomosis device 900 is configured in its low-profile delivery configuration, the measure of the angle at the vertex 918 between adjacent the struts 908 is less than the measure of the measure of the angle at the vertex 918 between adjacent the struts 908 when the anastomosis device 900 is configured in its deployed expanded configuration as shown. In some embodiments, the measure of the angle at the vertex 918 between adjacent the struts 908 decrease when the anastomosis device is configured in its low-profile delivery configuration. For example, the measure of the angle can be is less than 100°, e.g., less than 90°, less than 80°, less than 70°, less than 60°, less than 50°, less than 40°, less than 30°, less than 20°, less than 10°, and so forth. In some embodiments, the measure of the angle at the vertex 918 between adjacent the struts 908 decrease when the anastomosis device is configured in its low-profile delivery configuration. For example, the angle can be less than 100°, e.g., less than 90°, less than 80°, less than 70°, less than 60°, less than 50°, less than 40°, less than 30°, less than 20°, less than 10°, and so forth. The stability and support provided by the connecting member 910 serves to increase the apposition force provided against the gallbladder or provided against the portion of the gastrointestinal tract.

Figure 9B:
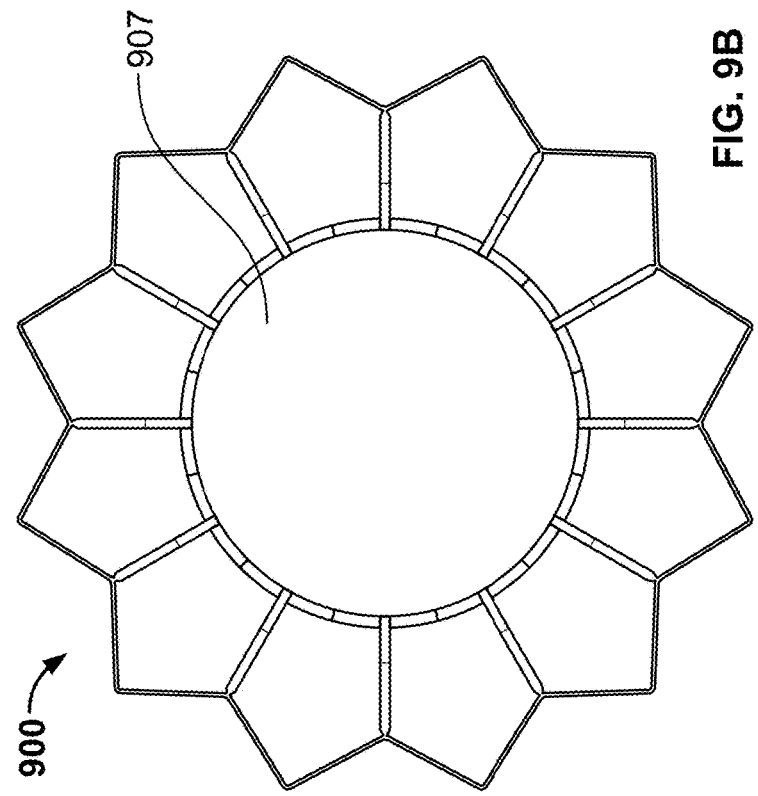
FIG. 9B is an end view of the anastomosis device of FIG. 9A.
Figure 9A:
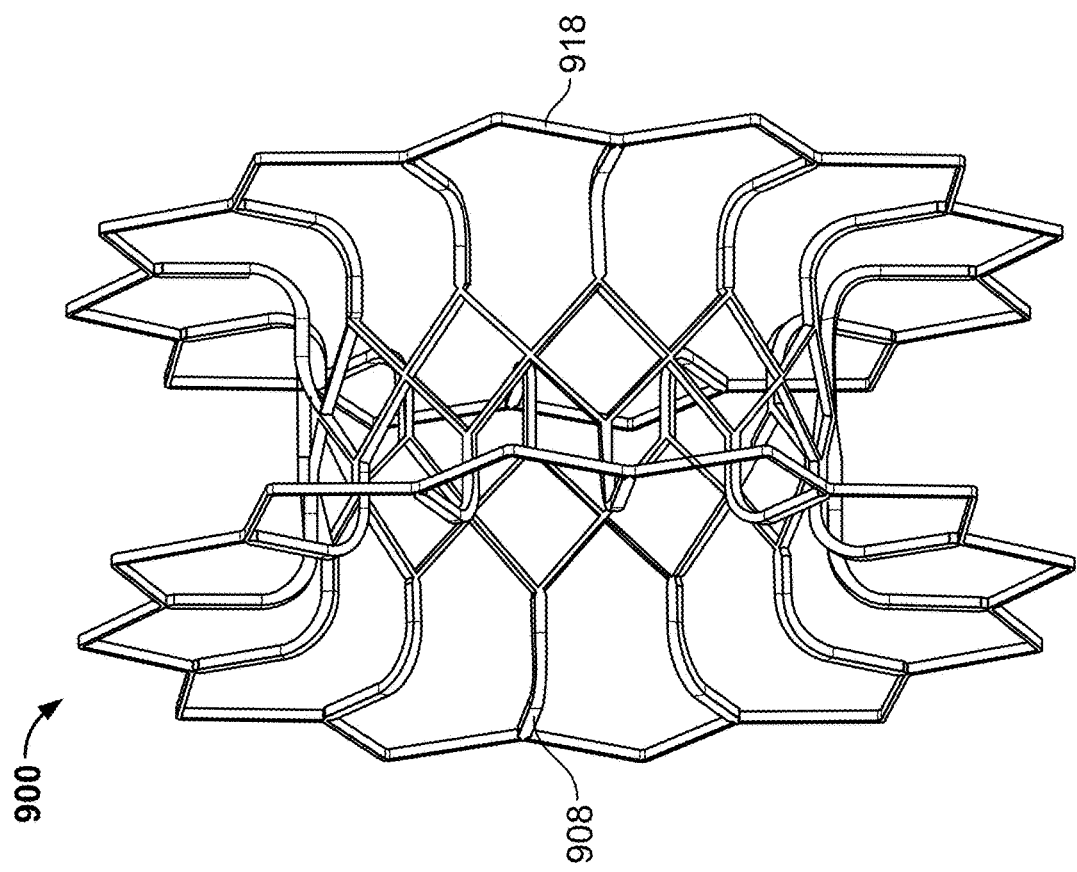
FIG. 9A is a perspective view of another exemplary anastomosis device in accordance with some embodiments.
Figure 9D:
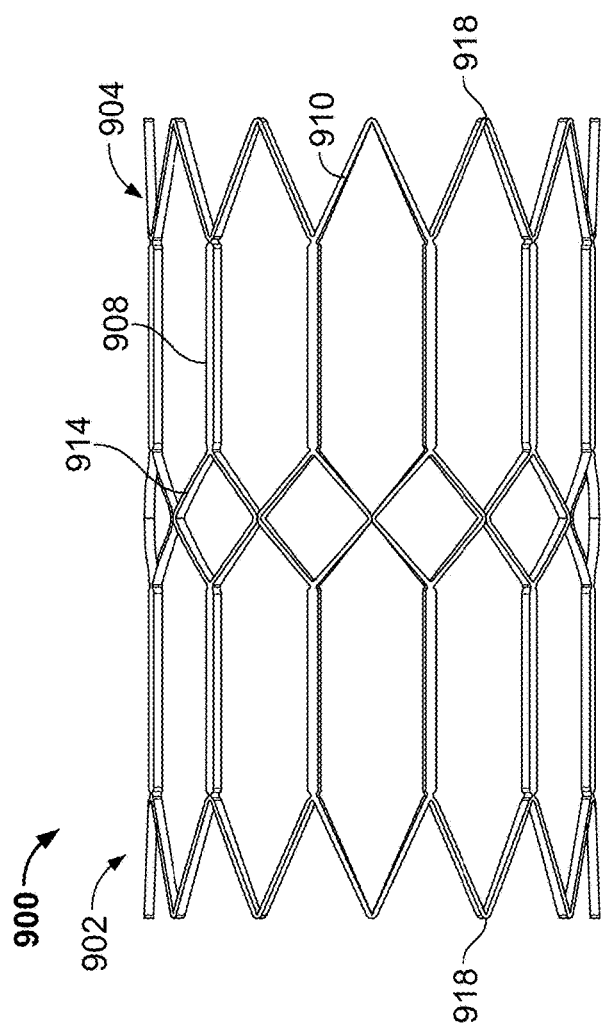
FIG. 9D is a side view of the framework of the anastomosis device of FIG. 9C before the flange structures are formed.
Figure 9E:
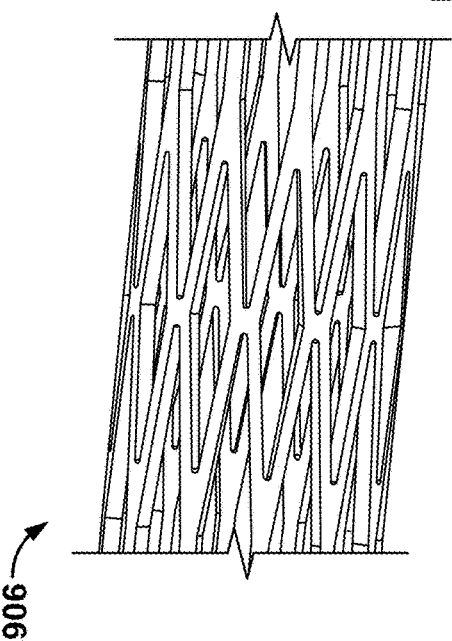
FIG. 9E is a perspective view of a center portion of the anastomosis device of FIG. 9C in a low-profile delivery configuration.

When the anastomosis device is configured in its low-profile delivery configuration, a cell 914 expands longitudinally (as shown in FIG. 9E) and, as the struts 908 are compressed towards the longitudinal axis, the distance between the adjacent vertices 918 is reduced. During deployment, the cell 914 expands radially (as shown in FIG. 9D), and the distance between the struts 908 increases. In some embodiments, the vertex 918 extends away from the central portion 906 as the adjacent vertex 918 is compressed together.

The connecting member 910, as described above, can comprise a variety of metallic shape memory materials and super-elastic alloys. Thus, the connecting member 910 can be configured to self-expand to an expanded deployed configuration, e.g., including a pre-determined angle of the vertex 918. The connecting member 910 typically operate from closed (nearly aligned) to open positions that can be around 90-100 degrees between them, but can be made to open less or more than 90-100 degrees in certain configurations.

Figure 9C:
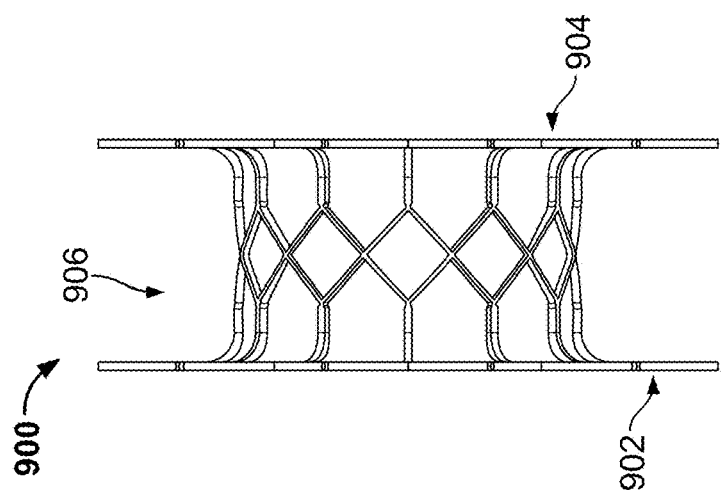
FIG. 9C is a side view of the anastomosis device of FIG. 9A.
Figure 10:
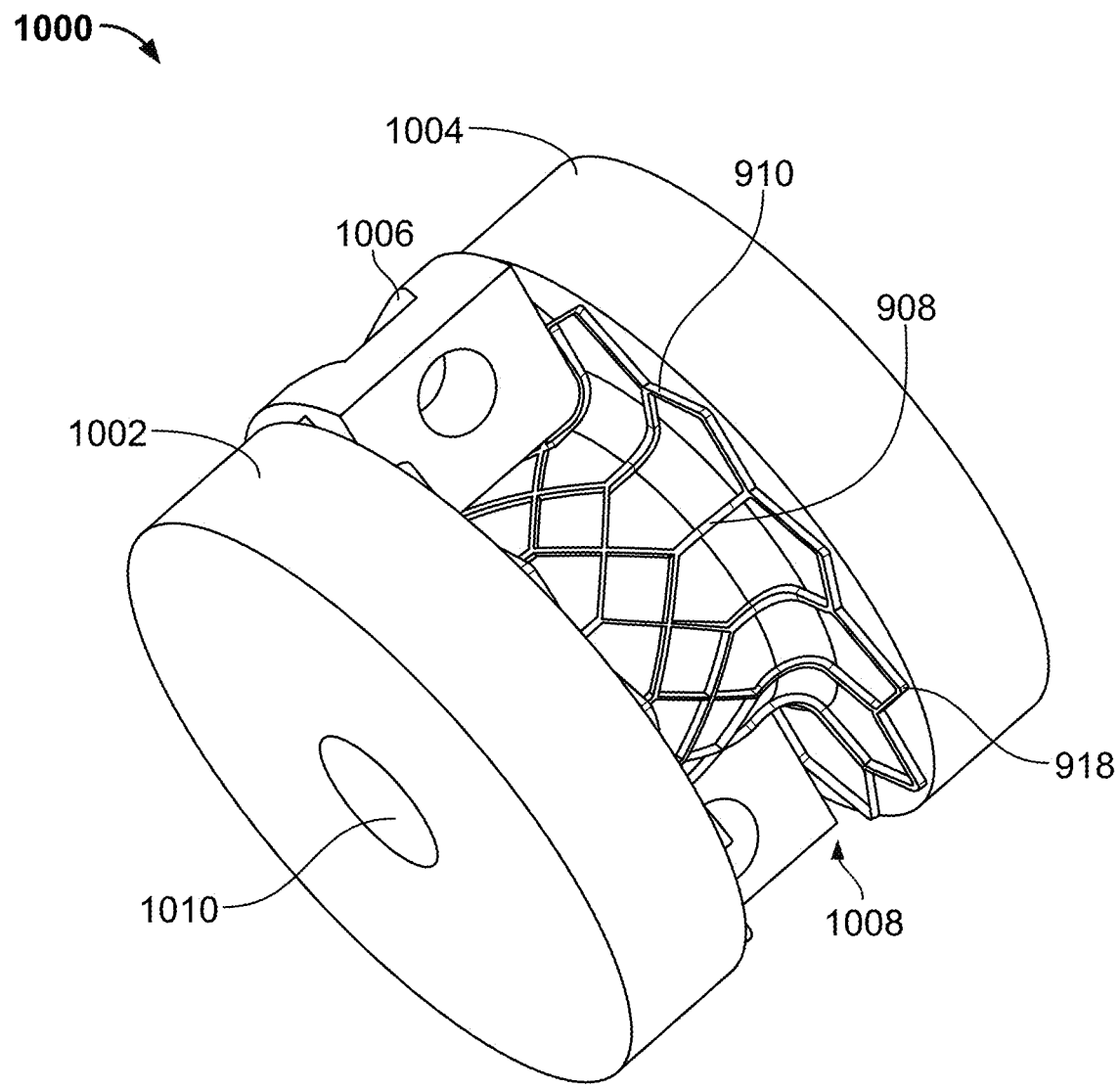
FIG. 10 is a perspective view of an anastomosis device on a forming mandrel in accordance with some of embodiments.

Referring to FIG. 10, an exemplary forming mandrel 1000 can be used to create some embodiments of the apposition portions of the anastomosis devices provided herein. For example, the forming mandrel 1000 can be used to create the frame as shown in FIGS. 9A, 9B, and 9C. The winding mandrel 1000 can be configured with the dimensional spacing, radii, and angles corresponding to the shape of the device 900 as desired. The forming mandrel 900 can also be readily modified to create other embodiments of devices having other configurations as desired.

In some embodiments, the mandrel 1000 includes two identical endplates 1002 and 1004, a shaft 1008, a central bore 1010, and a collar 1006. The endplates 1002, 1004, are oriented with the shaft 1008 such that the endplates 1002, 1004 oppose each other. In some embodiments, the endplates 1002, 1004 includes a locking mechanism, such as a setscrew, by which the endplates 1002, 1004 are releasably lockable to the shaft 1008. When the individual locking mechanisms are released, the individual endplates 1002 and/or 1004 can be axially translated, removed from the shaft 1008, and/or rotated in relation to the shaft 1008 and in relation to each other.

In some embodiments, after the device framework is mounted onto the mandrel 1000 as described above, the assembly is heated to shape-set the device to its configuration, e.g., a deployed or expanded configuration. In one such non-limiting example, the devise is laser cut from a NiTi tube, and the NiTi tube in an expanded state on the mounting mandrel 1000 is heated at about 470° C. for about 8 minutes. In other embodiments, higher or lower temperatures and shorter or longer times are used. The heating process will cause the laser cut NiTi tube to be heat-set into the deployed shape or the memory shape. Accordingly, the laser cut NiTi tube will tend to naturally self-expand to reconfigure itself to the memory shape when deployed from a delivery sheath to a target site within a body. In some embodiments, only a portion of the device is heated to a memory shape. For example, only the apposition portions 902 and/or 904, or the struts 908 are heated.

In some embodiments, a diameter of the shaft 1008 is the desired deployed diameter of the central portion 906. To mount the device framework, at least one endplate 1002 or 1004 is removed from the shaft 1008 and the shaft 1008 is inserted into the lumen of the framework. The removed endplate is re-attached to the shaft 1008 such that distance between the two endplates 1002 and 1004 is approximately equal to the desired length of the central portion 906 of the device. This distance causes end regions of the device to press against the endplates 1002 and 1004 and causes the struts 908 to bend and causes the connecting member 910 to extend from the longitudinal axis of the device at an angle of about 90°. The collar 1004 can be secured around the mounted device framework (as shown) to constrain the framework in the desired configuration until forming is complete.

Figure 11A:
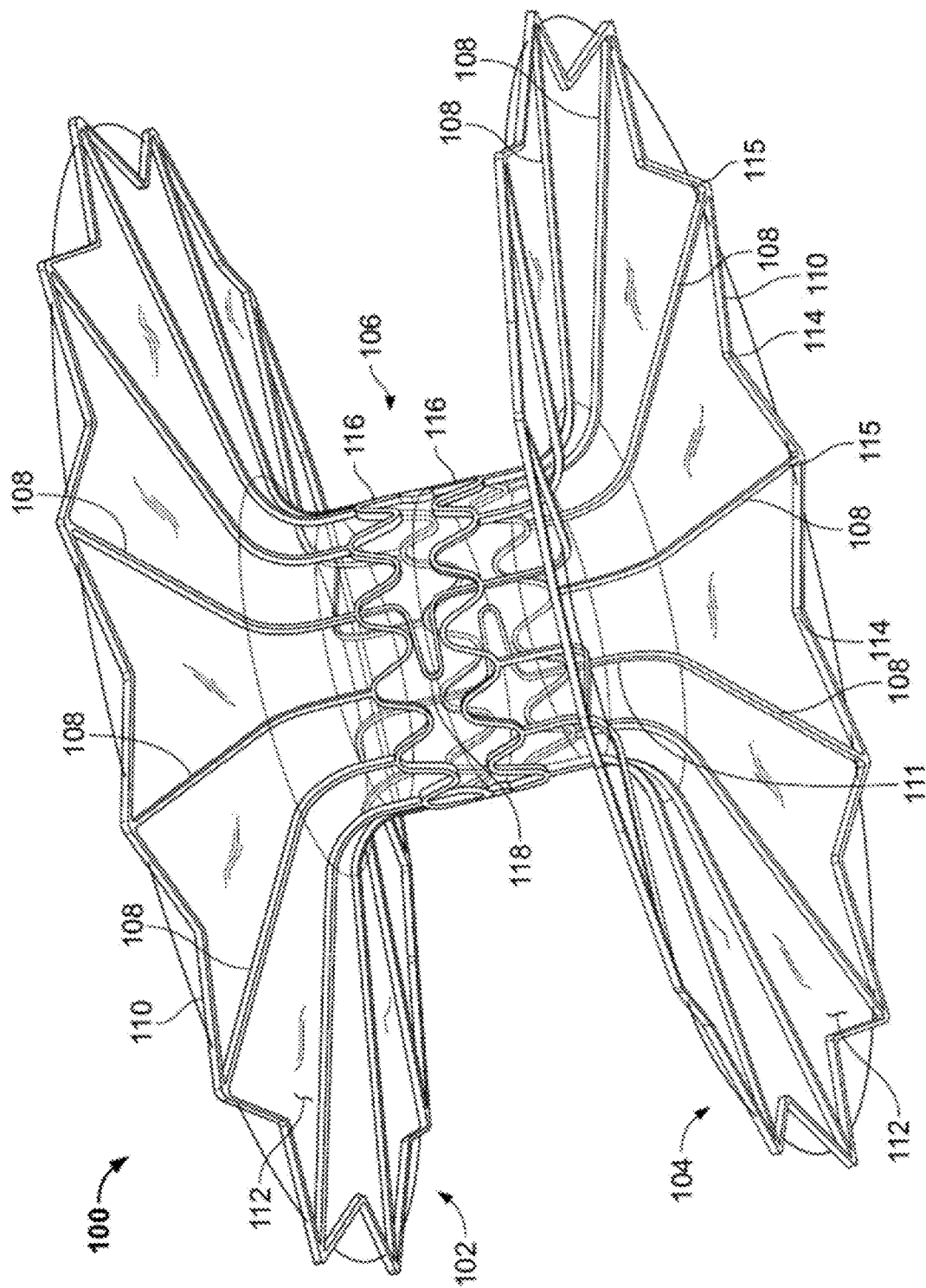
FIG. 11A is a perspective view of another exemplary anastomosis device in accordance with some embodiments.
Figure 11B:
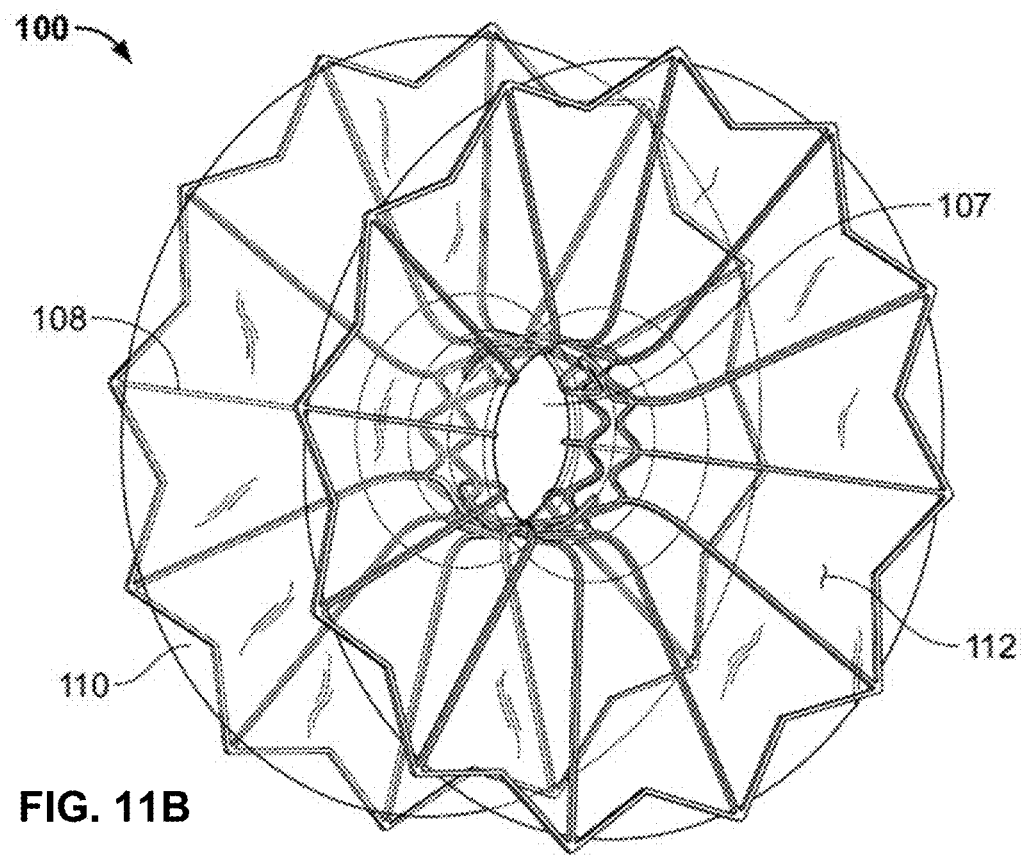
FIG. 11B is another perspective view of the anastomosis device of FIG. 11A.
Figure 11C:
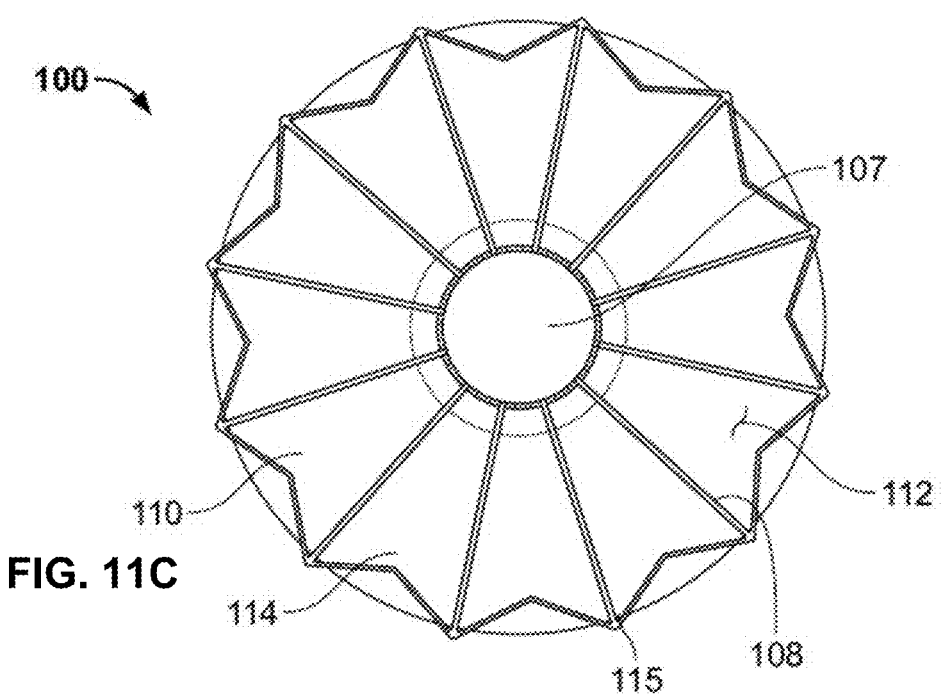
FIG. 11C is an end view of the anastomosis device of FIG. 11A.

Referring to FIGS. 11A-11C, an exemplary anastomosis device 100 includes a framework of elongate elements that defines a first apposition portion 102, a second apposition portion 104, and a central portion 106. The central portion 106 is disposed between and interconnects the first apposition portion 102 and the second apposition portion 104. A covering material 112 is disposed on at least some portions of the framework. Such a covering material (e.g., covering material 112 and others described below) may also be referred to herein merely as a covering.

In some embodiments, the central portion 106 defines a lumen 107 that extends between the first apposition portion 102 and the second apposition portion 104. In some implementations, the lumen 107 provides an anastomosis passageway (i.e., a tunnel) through which biological materials or liquids can pass. The device 100 is shown in an expanded configuration (also referred to herein as a deployed configuration). The expanded or deployed configuration is the configuration that the device 100 naturally exhibits in the absence of external forces acting upon the device 100. In should be understood that when the anastomosis device 100 is implanted in a patient, the configuration of the device 100 may be somewhat different than shown because of the external forces from the patient's anatomy that are exerted on the device 100.

The framework of anastomosis device 100 can be made using any of the materials and techniques as described above in reference to other anastomosis devices. In some embodiments, the first apposition portion 102, the second apposition portion 104, and the central portion 106, comprise a framework of interconnected elongate elements that is constructed by cutting a tube or a sheet. In some such embodiments, a tube of metallic material (e.g., nitinol, stainless steel, cobalt, etc.) is laser cut, and then the tube is expanded and shaped into the desired configuration. In some embodiments, the metallic material is shape-set in the desired configuration so that the material receives a shape-memory whereby the material will naturally strive to attain the desired configuration. In some embodiments, shape memory materials such as nitinol may strive to attain the desired configuration when exposed to body temperature.

In some embodiments, a covering material 112 can be disposed on some portions or on all of the first apposition portion 102, the second apposition portion 104, and/or the central portion 106. In some embodiments, portions of the first apposition portion 102, the second apposition portion 104, and/or the central portion 106 can remain free of the covering material 112.

The first apposition portion 102 and the second apposition portion 104 each include a plurality of struts 108. In some embodiments, the struts 108 of each of the first and second apposition portions 102 and 104 are configured to form, in a general sense, discs that contact tissue surfaces. More particularly, the first apposition portion 102 and the second apposition portion 104 are configured to engage one or more layers of tissue therebetween, and to provide apposition forces against the tissue surfaces. The apposition forces provided by the first and second apposition portions 102 and 104 can facilitate fixation of the device 100 to the tissue and provide migration resistance such that the device 100 can reliably remain positioned at a target site in a patient as desired.

In some embodiments, the materials and configuration of the anastomosis device 100 (and the other anastomosis device embodiments provided herein) allow the devices to be elastically crushed, folded, and/or collapsed into a low-profile delivery configuration for containment within a lumen for transcatheter or endoscopic/thorascopic delivery, and to self-expand to an operative size and configuration once positioned at a desired target site within a body and deployed from the lumen. For example, the anastomosis device 100 can be configured in a collapsed delivery configuration in which the plurality of struts 108 are radially compressed such that they are forced to extend substantially parallel to axis of the central portion 106, and in which the diameter of the central portion 106 is also crushed to become smaller. Due to the use of such materials and structure, the device 100 may also exhibit, for example, beneficial fatigue resistance and elastic properties.

After deployment, the plurality of struts 108 extend from the central portion 106 at a radial orientation and geometry to exert a desired level of apposition pressure on the tissue. In some embodiments, the plurality of struts 108 extend from the central portion 106 such that the nominal measure of the angle between the struts 108 and the longitudinal axis of the device 100 is about 100°, or about 90°, or about 80°, or about 70°, or about 60°, or about 50°, or about 40°, or about 30°, or about 20°, or about 10°, and the like. In some embodiments, the plurality of struts 108 extend from the central portion 106 such that the nominal measure of the angle between the struts 108 and the longitudinal axis of the device 200 is in a range from about 80° to about 100°, or about 70° to about 90°, or about 60° to about 80°, or about 50° to about 70°, or about 40° to about 60°, or about 30° to about 50°, or about 20° to about 40°, or about 10° to about 30°.

Still referring to FIGS. 11A-11C, in some embodiments of the anastomosis device 100 (and in some embodiments of the other anastomosis devices provided herein) the plurality of struts 108 are interconnected by connecting members 110. The connecting members 110 are shown in deployed configurations in which the connecting members 110 are arranged in a series of undulations—each having a vertex 114 extending towards the central portion 106 and a vertex 115 extending away from the central portion 106. In some embodiments, the connecting members 110 serve to support and stabilize the struts 108 to thereby cause the apposition portions 102 and 104 to have a more rigid construct. In some such embodiments, the apposition portions 102 and 104 can exert a greater level of apposition pressure while maintain a compliancy by which the apposition portions 102 and 104 can conform to the anatomical topography of the tissue. In addition, the sealing capabilities of the apposition portions 102 and 104 may be enhanced. The stability and support provided by the connecting member 110 serves to increase the apposition force provided against the gallbladder or provided against the portion of the gastrointestinal tract.

While in the depicted embodiment the connecting members 110 are a series of generally linear segments that are joined to form a chevron between adjacent struts 108, in some embodiments the connecting members 110 comprise a continuous wavy or sinusoidal configuration (e.g., a sine wave). For example, in some embodiments the connecting members 110 may be linear between the struts 108 when the anastomosis device 100 is in its deployed configuration. While in the depicted embodiment, the connecting members 110 extend from the radial ends of the struts 108, in some embodiments the connecting members 110 may be attached to or extend from the struts 108 at other locations on the struts 108. In some embodiments, two or more sets of connecting members 110 can be included (extending from one or more of the struts 108).

When the anastomosis device 100 is configured in its low-profile delivery configuration, the measure of the angle defined by the vertices 114 and 115 is less than the measure of the angle defined by the vertices 114 and 115 when the anastomosis device 100 is configured in its deployed expanded configuration as shown. Said another way, as the struts 108 are compressed towards the device's longitudinal axis, the distance between the adjacent vertices 114 and 115 is reduced. In some embodiments, each vertex 114 extends towards the central portion 106 and each vertex 115 extends away from the central portion 106 when the anastomosis device 100 is in the collapsed low-profile delivery configuration.

The connecting member 110, as described above, can comprise a variety of materials including, but not limited to, metallic shape memory materials and super-elastic alloys. Thus, the connecting members 110 can be configured to self-expand to an expanded deployed configuration, e.g., including to a pre-determined angle of the vertices 114 and 115.

Figure 11D:
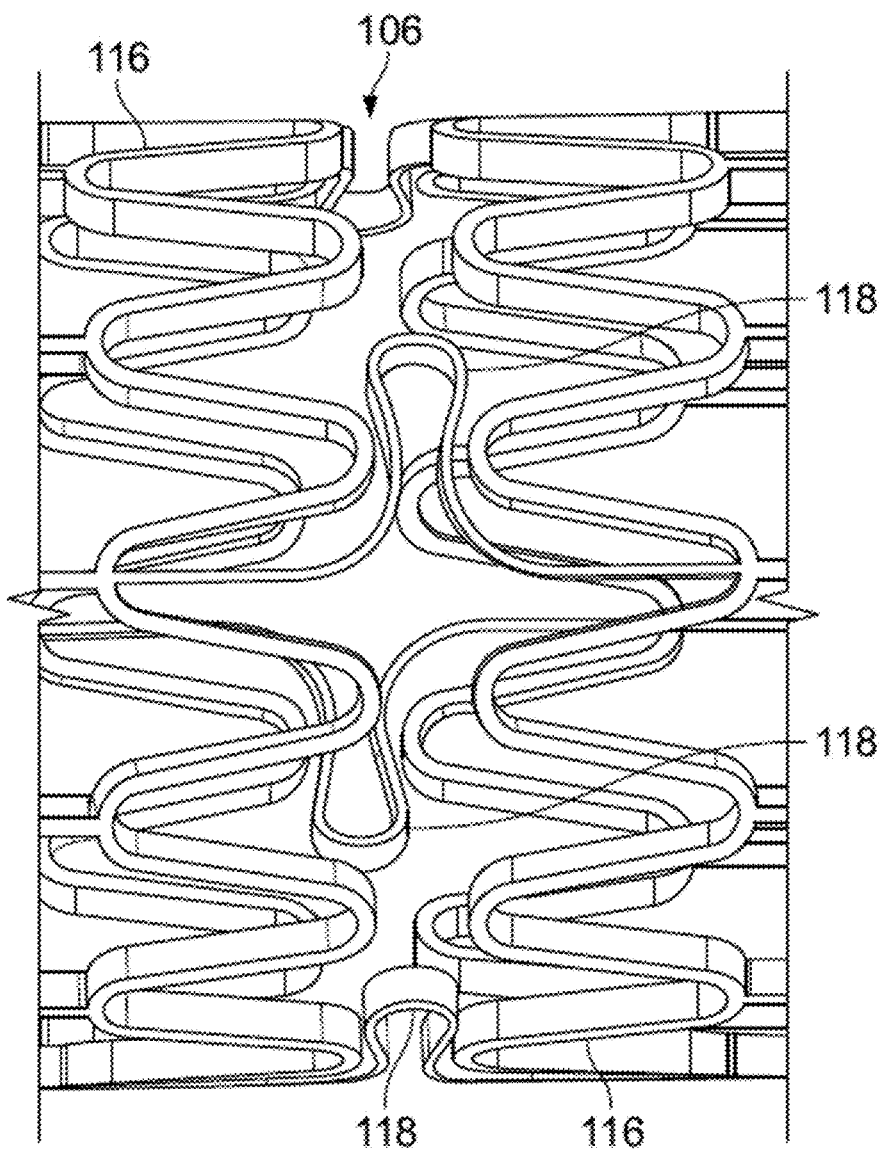
FIG. 11D is a side view of a central portion of the anastomosis device of FIG. 11A that includes an expansion member in accordance with some embodiments.

Referring also to FIG. 11D, the central portion 106 includes one or more circumferential stent rings 116 and one or more axial adjustment members 118. It should be understood that for enhanced visibility, the central portion 106 is shown in FIG. 11D without a covering material. The axial adjustment members 118 interconnect the stent rings 116. Using this construct, the central portion 106 is configured to axially expand or contract in response to tensile forces transferred to the central portion 106 from the apposition portions 102 and 104. Such forces can be the result of the apposition pressure applied to tissue(s) compressed between the apposition portions 102 and 104. Said another way, the axial adjustment members 118 can act as suspension springs so that the anastomosis device 100 can axially extend or contract to accommodate various thicknesses of tissue between the apposition portions 102 and 104. This feature can be advantageous, for example, because tissue may be thicker when it is inflamed, and may become thinner as it returns to normal (heals). In such a case, the anastomosis device 100 can automatically adjust in response to varying tissue thicknesses throughout the healing process.

In the depicted embodiment, two stent rings 116 are included. In some embodiments, fewer or more than two stent rings 116 can be included. In the depicted embodiment, the stent rings 116 are aligned with each other. That is, the peaks and/or valleys of each individual stent ring 116 is positioned in axial alignment with the peaks and/or valleys of the other individual stent ring 116. However, such alignment is not required in all embodiments. In the depicted embodiment, the stent rings 116 exhibit a pattern of peaks and valleys in a sinusoidal-like pattern. However, it should be clear that the stent rings 116 can be configured to have any other suitable geometry. For example, a serpentine pattern or a pattern of closed rhombus-shaped cells are suitable in some embodiments. The stent rings 116 are interconnected to each other by at least one axial adjustment member 118, and the stent rings 116 are connected to the struts 108 of the apposition portions 102 or 104.

The central portion 106 is shown in a deployed or expanded configuration. In some embodiments, the central portion 106, as described above, can comprise a variety of metallic shape memory materials and super-elastic alloys. Thus, the central portion 106 can be configured to self-expand to the deployed configuration. In some embodiments, the central portion 106 is balloon expandable to the deployed configuration, or supplemental expansion forces can be applied to a self-expandable device by balloon dilation. The diameter of the central portion 106 can be made in any size as desired in order to suit the intended use and/or delivery system of the anastomosis device 100. For example, in the low-profile delivery configuration the anastomosis device 100 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. When the anastomosis device 100 is configured in its expanded deployed configuration as shown, the diameter of the central portion 106 increases to a deployed diameter. In some implementations, the deployed outer diameter of the central portion 106 is configured to at least partially anchor the device 100 via an interference fit with the tissue aperture in which the central portion 106 resides. However, in some implementations the deployed outer diameter of the central portion 106 is slightly less than the diameter of the tissue aperture in which the central portion 106 resides, and the apposition portions 102 and 104 compress the tissue to provide the migration resistance. In some embodiments, the fully expanded diameter of the central portion 106 is about 30 mm, or about 25 mm, or about 20 mm, or about 15 mm, or about 12 mm, or about 10 mm, or about 8 mm, or about 6 mm, or about 4 mm, and the like. In some embodiments, the fully expanded diameter of the central portion 106 is in a range between about 20 mm to about 30 mm, or about 15 mm to about 25 mm, or about 10 mm to about 20 mm, or about 5 mm to about 15 mm, or about 4 mm to about 8 mm, and the like.

The one or more axial adjustment members 118 are disposed within the central portion 106 so as to interconnect the stent rings 116. In some embodiments, the axial adjustment members 118 are configured in an undulating or horseshoe-like shape (not shown). The undulations of the axial adjustment member 118 extend in directions so that the central portion 106 can axially extend as a result of axially extending the axial adjustment members 118 (e.g., by causing the axial adjustment members 118 to become more linear). The undulations of the axial adjustment members 118 provide a store of excess material and/or mechanical energy to facilitate the expansion or contraction of the axial length of the device 100.

The length of the central portion 106 can be made in any dimension as desired in order to suit the intended use and/or delivery system of the anastomosis device 100. The inclusion of the one or more axial adjustment members 118 can allow the anastomosis device 100 to be useable over a range of tissue thicknesses, and can advantageously improve contact between the tissues for enhancing anastomosis performance. In some embodiments, the adjacent stent rings 116 can be longitudinally separated from each other until the device reaches an axial adjustment limit, e.g., until the axial adjustment members 118 appear as a substantially straight line.

In some implementations, the axial length of the device is at least somewhat adjusted before or during deployment, e.g., by a clinician to accommodate particular tissue thicknesses at a target implant site. In other example implementations, the axial adjustment members 118 automatically responds to mechanical forces exerted on the deployed device 100 in situ. For example, the axial adjustment members 118 may permit the axial length of the device 100 to dynamically adjust during deployment and/or during the tissue healing process. In one such example implementation in which an anastomosis is created between a gallbladder and a duodenum, the gallbladder (if inflamed) can have an initial wall thickness that later reduces when the inflammation subsides. The axial adjustment members 118 can permit the axial length of the device 100 to dynamically adjust from the initial thickness to the later thickness as the inflammation of the gallbladder wall subsides.

The anastomosis device 100 also includes the covering material 112. The covering material 112 can be constructed of any of the materials and using any of the techniques described above in reference to the covering materials of the other anastomosis devices provided herein. In some embodiments, the covering material 112 is disposed on at least some portions (or on all) of the first apposition portion 102, the second apposition portion 104, and the central portion 106. In some embodiments, some portions of the first apposition portion 102, the second apposition portion 104, and/or the central portion 106 are not covered by the covering material 112.

Figure 12:
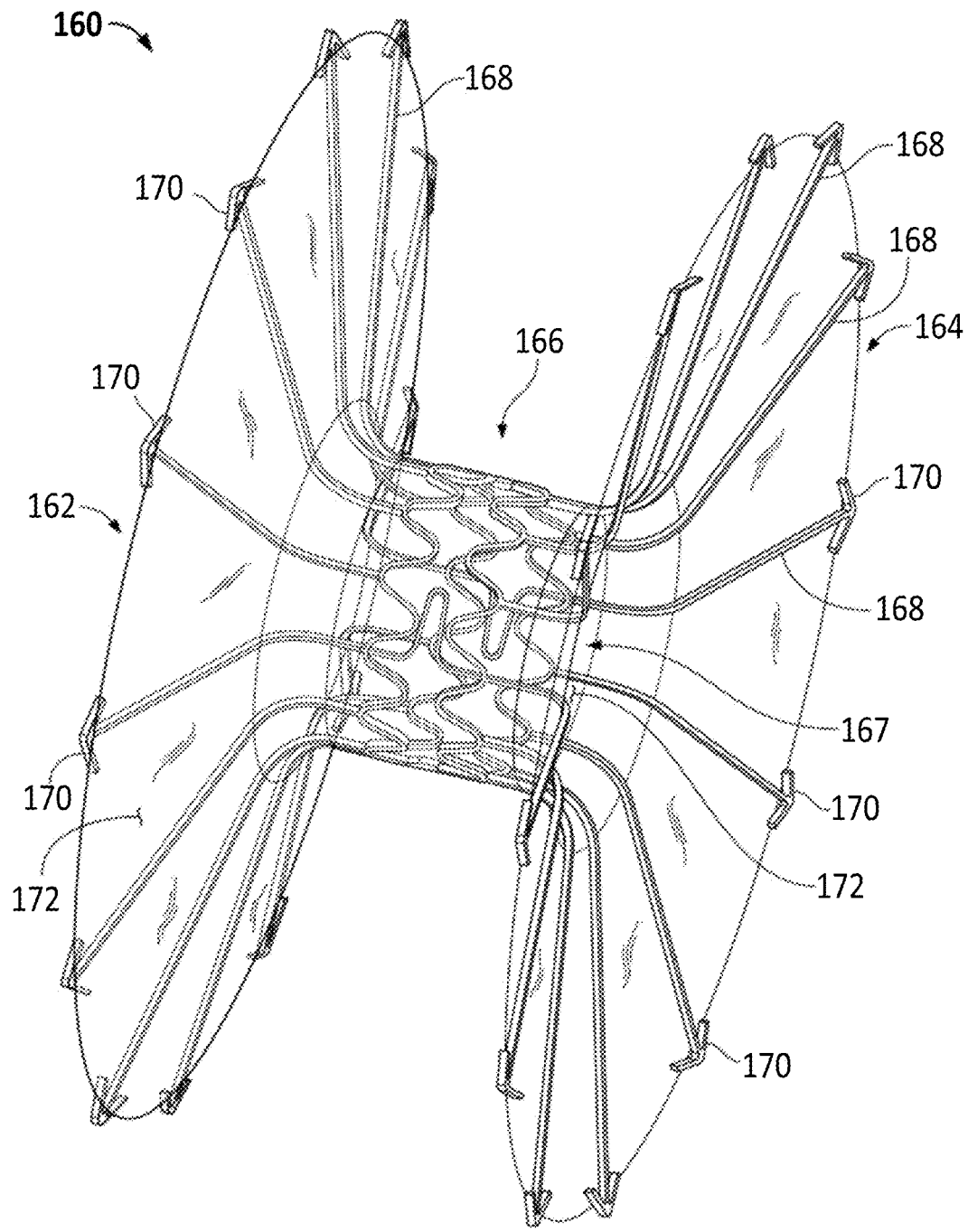
FIG. 12 is a perspective view of another exemplary anastomosis device in accordance with some embodiments.

Referring to FIG. 12, another exemplary anastomosis device 160 includes a framework of elongate elements that defines a first apposition portion 162, a second apposition portion 164, and a central portion 166. The central portion 166 is disposed between and interconnects the first apposition portion 162 and the second apposition portion 164. A covering material 172 is disposed on at least some portions of the framework. In some embodiments, the central portion 166 defines a lumen 167 that extends between the first apposition portion 162 and the second apposition portion 164. In some implementations, the lumen 167 provides an anastomosis passageway or tunnel through which biological materials or liquids can pass. The device 160 is shown in an expanded configuration. The expanded configuration is the configuration that the device 160 naturally exhibits in the absence of external forces acting upon the device 160.

The materials, configurations, and techniques for construction of the anastomosis device 160 can be the same as those described above in reference to the other anastomosis devices provided herein. In some embodiments, the anastomosis device 160 does not include elongate elements that interconnect the struts 168 (in contrast to the connecting members 110 that interconnect the struts 108 of the anastomosis device 100).

In some embodiments, the anastomosis device 160 can be constructed to have a tailored radial strength by varying design parameters such as the number of cells, tube thickness, cell geometry, covering material, and the like. For example, in anastomosis device applications the central portion 166 is designed to have a radial strength that is resistant to circumferential loading from the surrounding tissue. The radial strength of some such anastomosis devices facilitates the remodeling of the tissue external to the lumen, and can cause the tissue to have a lumen size that approximates the lumen size of the device.

In some embodiments, the free ends of one or more of the struts 168 include a member 170. In some embodiments, the member 170 can include an anchor, barb, protrusion, atraumatic member, and/or a support scaffold for the covering material 172. In some embodiments two or more struts 168 includes members 170 that have the differing configurations. In some embodiments, each of the struts 168 have members 170 with the same configuration.

It should be understood that one or more design features of the anastomosis devices provided herein can be combined with other features of other anastomosis devices provided herein. In effect, hybrid designs that combine various features from two or more of the anastomosis device designs provided herein can be created, and are within the scope of this disclosure.

In some embodiments the devices provided herein can be used for sealing or anchoring a heart valve implant. A heart valve implant enables one-way flow of blood from a heart chamber and usually has a first inflow end and a second outflow end. The contractions of the heart cause flow of blood through the valve from the inflow end to the outflow end. Between the inflow and outflow ends, a valve assembly within the heart valve implant provides for one way flow, opening to allow flow from the inflow to the outflow end when the pressure of the blood is higher on the inflow end, and closing to prevent flow when the pressure on the outflow end is higher than the inflow end. In some embodiments, the device includes a tunnel or central aperture through the device with apposition portions to anchor a valve assembly and seal against backward flow. A valve assembly can be attached in the tunnel or central aperture. The apposition portions of the device can be configured to be highly conformable to the topography of the heart chambers or blood vessels, and compliant with the beating movements of the heart. In some embodiments, a covering material is configured to allow flow through a valve assembly in the tunnel or aperture while preventing flow around the apposition portions.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device comprising:
   a tubular structure comprising at least one elongate member forming a framework of interconnected struts, the tubular structure including:
   a central portion defining a longitudinal axis and including a plurality of central portion cells defined by the at least one elongate member, wherein the central portion cells are open to longitudinally-adjacent central portion cells and are closed to circumferentially-adjacent central portion cells;
   a first apposition portion at a first end of the central portion, the first apposition portion comprising a plurality of first flange cells defined by the at least one elongate member;
   a second apposition portion at a second end of the central portion, the second apposition portion comprising a plurality of second flange cells defined by the at least one elongate member, wherein at least some of the second flange cells are closed at a first end by an undulating portion of the at least one elongate member and opened at a second end to the central portion; and
   a covering material configured to be at least partially disposed on at least one of the central portion, the first apposition portion, and the second apposition portion.

2. The device of claim 1, wherein the at least one elongate member forms a first pattern extending longitudinally along the central portion, a first flange cell of the plurality of first flange cells, a second pattern extending longitudinally along the central portion, the second pattern opposing the first pattern, a second flange cell of the plurality of second flange cells.

3. The device of claim 2, wherein the at least one elongate member comprises a single elongate member that forms the central portion, the first apposition portion, and the second apposition portion.

4. The device of claim 1, wherein the at least one elongate member forms a pattern so as to first define a first flange cell of the plurality of first flange cells, the elongate member second traverses the central portion, the elongate member third defines a second flange cell of the plurality of second flange cells, the elongate member fourth traverses the central portion, and thereafter the elongate member repeats the pattern to form additional flange cells of the first and second plurality of flange cells while traversing the central portion in between.

5. The device of claim 4, wherein each successive flange cell of the first and second plurality of flange cells is out of phase with directly preceding flange cells of the first and second plurality of flange cells.

6. The device of claim 1, wherein each first flange cell of the plurality of first flange cells is open to a respective central portion cell of the plurality of central portion cells, and wherein each second flange cell of the plurality of second flange cells is open to another respective central portion cell of the plurality of central portion cells.

7. The device of claim 1, wherein each of the plurality of second flange cells is open to one or more of the central portion cells of the plurality of central portion cells.

8. The device of claim 1, wherein the undulating portion is sinusoidal.

9. The device of claim 1, wherein each of the first and second apposition portions comprises circumferential rings that undulate substantially sinusoidally along edges thereof.

10. The device of claim 1, wherein the central portion cells are open to a gap between struts of at least one of the first and second apposition portions.

11. The device of claim 1, wherein the central portion comprises a plurality of body struts each comprising a plurality of longitudinally-extending portions interconnected with a plurality of angled portions that combine to define the plurality of central portion cells without interconnecting adjacent body struts across the central portion cells along the length of the body struts.

12. The device of claim 1, wherein the covering material inhibits tissue ingrowth into the covering material.

13. The device of claim 1, wherein at least a portion of the covering material comprises a microporous structure to provide a tissue ingrowth scaffold.

14. The device of claim 1, wherein the covering material is configured to release a pharmacological agent to promote tissue ingrowth.

15. The device of claim 14, wherein the pharmacological agent is covalently attached to the covering material.

16. The device of claim 14, wherein the covering material is impregnated with the pharmacological agent.

17. The device of claim 1, wherein the framework of interconnected struts is compressible to extend substantially parallel to the central portion.

18. The device of claim 1, wherein the framework of interconnected struts is compressible into a low-profile configuration for containment within a catheter for delivery and is also self-expandable to an operative size when deployed from the catheter.

19. An implantable medical device comprising:
a tubular structure comprising at least one elongate member forming a framework of interconnected struts, the tubular structure defining:
a central portion comprising a plurality of body cells defined by the at least one elongate member, wherein the central portion comprise a plurality of body struts each having a plurality of axially-extending portions interconnected with a plurality of angled portions that combine to define the plurality of body cells without interconnecting adjacent body struts across the body cells along the length of the body struts;
a first apposition portion at a first end of the central portion having a plurality of first flange cells defined by the at least one elongate member such that the plurality of first flange cells are open to the central portion; and
a second apposition portion at a second end of the central portion comprising a plurality of second flange cells defined by the at least one elongate member such that the plurality of second flange cells are open to the central portion,
wherein the framework of interconnected struts is compressible into a low-profile configuration for delivery and is also self-expandable to an operative size.

20. The device of claim 19, wherein the at least one elongate member is formed such that the at least one elongate member forms a first pattern traversing the central portion along a longitudinal axis, the elongate member defines a first flange cell of the plurality of first flange cells, the elongate member traverses the central portion along the longitudinal axis in a second pattern opposing said first pattern, and the elongate member defines a second flange cell of the plurality of second flange cells.

21. The device of claim 19, wherein the at least one elongate member is formed in a pattern so as to first define a first flange cell of the plurality of first flange cells, the elongate member second traverses the central portion, the elongate member third defines a second flange cell of the plurality of second flange cells, the elongate member fourth traverses the central portion, and thereafter the elongate member repeats the pattern to form additional flange cells of the first and second plurality of flange cells while traversing the central portion in between.

22. The device of claim 19, wherein the body cells are open to longitudinally-adjacent body cells and are closed to circumferentially-adjacent body cells, wherein each of the plurality of first and second flange cells is open to one or more of the plurality of body cells.

23. The device of claim 19, wherein each of the first and second apposition portions comprises circumferential rings that undulate substantially sinusoidally along edges thereof.

24. An implantable medical device comprising:
a tubular structure comprising at least one elongate member forming a framework of interconnected struts, the tubular structure defining:
a central portion having a plurality of body cells defined by the at least one elongate member;
a first apposition portion at a first end of the central portion having a plurality of first flange cells defined by the at least one elongate member; and
a second apposition portion at a second end of the central portion having a plurality of second flange cells defined by the at least one elongate member, wherein the framework of interconnected struts is compressible to extend substantially parallel to the central portion, wherein the at least one elongate member is formed such that the at least one elongate member forms a first pattern traversing the central portion along a longitudinal axis, the elongate member defines a first flange cell of the first plurality of flange cells, the elongate member traverses the central portion along the longitudinal axis in a second pattern opposing said first pattern, and the elongate member defines a second flange cell of the second plurality of flange cells,
wherein each successive flange cell of the first and second plurality of flange cells is out of phase with directly preceding flange cells of the first and second plurality of flange cells, wherein the body cells are open to longitudinally-adjacent body cells and are closed to circumferentially-adjacent body cells, and wherein each of the plurality of first flange cells is open to the central portion and each of the plurality of second flange cells is open to the central portion.

* * * * *